United States Patent [19]
Christensen, IV et al.

[11] Patent Number: 5,891,883
[45] Date of Patent: Apr. 6, 1999

[54] 4,4-(DISUBSTITUTED)CYCLOHEXAN-1-OLS MONOMERS AND RELATED COMPOUNDS

[75] Inventors: Siegfried B. Christensen, IV, Philadelphia; Joseph M. Karpinski; M. Dominic Ryan, both of Pottstown, all of Pa.; Paul E. Bender, Cherry Hill, N.J.

[73] Assignee: SmithKline Beecham Corporation, Philadelphia, Pa.

[21] Appl. No.: 860,287

[22] PCT Filed: Dec. 21, 1995

[86] PCT No.: PCT/US95/16711

§ 371 Date: Sep. 11, 1997

§ 102(e) Date: Sep. 11, 1997

[87] PCT Pub. No.: WO96/19988

PCT Pub. Date: Jul. 4, 1996

[51] Int. Cl.$^6$ ............ A61K 31/38; A61K 31/435; C07D 239/02; C07D 271/06
[52] U.S. Cl. .......... 514/269; 514/277; 514/363; 514/438; 544/332; 546/334; 546/344; 548/131; 548/136; 549/61; 564/443
[58] Field of Search .................. 514/269, 277, 514/363, 438; 546/334, 344; 549/61; 548/131, 136; 544/332; 564/443

[56] References Cited

U.S. PATENT DOCUMENTS

| | | | |
|---|---|---|---|
| 5,449,687 | 9/1995 | Christensen et al. | 514/520 |
| 5,602,157 | 2/1997 | Christensen, IV et al. | 514/362 |
| 5,602,173 | 2/1997 | Christensen, IV et al. | 514/475 |
| 5,605,923 | 2/1997 | Christensen, IV et al. | 514/417 |
| 5,614,540 | 3/1997 | Christensen, IV et al. | 514/362 |
| 5,643,946 | 7/1997 | Christensen, IV et al. | 514/512 |

OTHER PUBLICATIONS

Psotta et al., J. Chem. Soc., Perkin Transactions I, (1979), (4), 1063–1065, "Joubertinamine: A Novel seco–Mesembrane Alkaloid".

Christensen et al., Chemical Abstracts, 126:117989 (1997).

*Primary Examiner*—Fiona T. Powers
*Attorney, Agent, or Firm*—James M. Kanagy; Stephen Venetianer

[57] ABSTRACT

The present invention relates to 4,4(disubstituted) cyclohexan-1-ol monomers and related compounds, pharmaceutical compositions containing these compounds, and their use in treating allergic and inflammatory diseases and for inhibiting the production of Tumor Necrosis Factor (TNF).

9 Claims, No Drawings

4,4-(DISUBSTITUTED)CYCLOHEXAN-1-OLS MONOMERS AND RELATED COMPOUNDS

FIELD OF INVENTION

The present invention relates to novel 4,4-(disubstituted) cyclohexan-1-ols monomers and related compounds, pharmaceutical compositions containing these compounds, and their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3', 5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically *Candida albicans* has been shown to induce TNF production in vitro in human monocytes and natural killer cells. [See Riipi et al., Infection and Immunity, 58(9):2750–54, 1990; and Jafari et al., Journal of Infectious Diseases, 164:389–95, 1991. See also Wasan et al., Antimicrobial Agents and Chemotherapy, 35,(10):2046–48, 1991; and Luke et al., Journal of Infectious Diseases, 162:211–214, 1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

Compounds of the Formula (I):

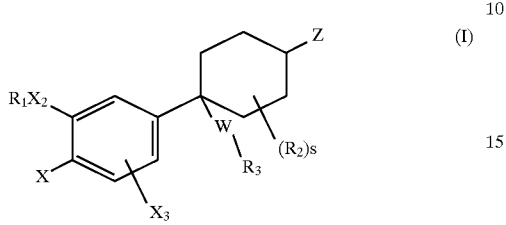

wherein:

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties unsubstituted or substituted with one or more halogens;

m is 0 to 2;

n is 0 to 4;

r is 0 to 6;

$R_4$ and $R_5$ are independently selected hydrogen or $C_{1-2}$ alkyl;

$R_6$ is hydrogen, methyl, hydroxyl, aryl, halo substituted aryl, aryloxy $C_{1-3}$ alkyl, halo substituted aryloxy $C_{1-3}$ alkyl, indanyl, indenyl, $C_{7-11}$ polycycloalkyl, tetrahydrofuranyl, furanyl, tetrahydropyranyl pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, one ethyl group, or an hydroxyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —$(CR_4R_5)_nO(CR_4R_5)_mR_6$;

X is $YR_2$, fluorine, $NR_4R_5$, or formyl amine;

Y is O or $S(O)_{m'}$;

m' is 0, 1, or 2;

$X_2$ is O or $NR_8$;

$X_3$ is hydrogen or X;

$X_4$ is H, $R_9$, $OR_8$, CN, $C(O)R_8$, $C(O)OR_8$, $C(O)NR_8R_8$, or $NR_8R_8$;

$R_2$ is independently selected from —$CH_3$ or —$CH_2CH_3$ optionally substituted by 1 or more halogens;

s is 0 to 4;

W is alkyl of 2 to 6 carbons, alkenyl of 2 to 6 carbon atoms or alkynyl of 2 to 6 carbon atoms;

$R_3$ is $COOR_{14}$, $C(O)NR_4R_{14}$ or $R_7$;

Z is $OR_{14}$, $OR_{15}$, $SR_{14}$, $S(O)_{m'}R_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$;

Y' is O or S;

$R_7$ is —$(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines, —F, —Br, —Cl, —$NO_2$, —$NR_{10}R_{11}$, —$C(O)R_8$, —$CO_2R_8$, —$O(CH_2)_{2-4}OR_8$, —$O(CH_2)_qR_8$, —CN, —$C(O)NR_{10}R_{11}$, —$O(CH_2)_qC(O)NR_{10}R_{11}$, —$O(CH_2)_qC(O)R_9$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, or $R_{13}$;

q is 0, 1, or 2;

$R_{12}$ is $R_{13}$, $C_3$–$C_7$ cycloalkyl, or an unsubstituted or substituted aryl or heteroaryl group selected from the group consisting of (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, and phenyl;

$R_8$ is independently selected from hydrogen or $R_9$;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised of carbon or carbon and one or more additional heteroatoms selected from O, N, or S;

$R_{13}$ is a substituted or unsubstituted heteroaryl group selected from the group consisting of oxazolidinyl, oxazolyl, thiazolyl, pyrazolyl, triazolyl, tetrazolyl, imidazolyl, imidazolidinyl, thiazolidinyl, isoxazolyl, oxadiazolyl, and thiadiazolyl, and where $R_{13}$ is substituted on $R_{12}$ or $R_{13}$ the rings are connected through a carbon atom and each second $R_{13}$ ring may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring comprised of carbon or carbon and one or more additional heteroatoms selected from O, N, or S;

$R_{15}$ is $C(O)R_{14}$, $C(O)NR_8R_{14}$, $S(O)_qNR_8R_{14}$ or $S(O)_qR_7$ where q is 0, 1 or 2;

provided that:
(f) $R_7$ is not $C_{1-4}$ alkyl unsubstituted or substituted by one to three fluorines;

or the pharmaceutically acceptable salts thereof.

This invention also relates to the pharmaceutical compositions comprising a compound of Formula (I) and a pharmaceutically acceptable carrier or diluent.

The invention also relates to a method of mediation or inhibition of the enzymatic activity (or catalytic activity) of PDE IV in mammals, including humans, which comprises administering to a mammal in need thereof an effective amount of a compound of Formula (I) as shown below.

The invention further provides a method for the treatment of allergic and inflammatory disease which comprises administering to a mammal, including humans, in need thereof, an effective amount of a compound of Formula (I).

The invention also provides a method for the treatment of asthma which comprises administering to a mammal, including humans, in need thereof, an effective amount of a compound of Formula (I).

This invention also relates to a method of inhibiting TNF production in a mammal, including humans, which method comprises administering to a mammal in need of such treatment, an effective TNF inhibiting amount of a compound of Formula (I). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I).

Compounds of Formula (I) are also useful in the treatment of additional viral infections, where such viruses are sensitive to upregulation by TNF or will elicit TNF production in vivo.

In addition, compounds of Formula (I) ate also useful in treating yeast and fungal infections, where such yeast and fungi are sensitive to upregulation by TNF or will elicit TNF production in vivo.

DETAILED DESCRIPTION OF THE INVENTION

This invention also relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of Formula (I).

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and central nervous system disorders such as depression and multi-infarct dementia.

The viruses contemplated for treatment herein are those that produce TNF as a result of infection, or those which are sensitive inhibition, such as by decreased replication, directly or indirectly, by the TNF inhibitors of Formula (I). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (I).

The compounds of this invention may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, the compounds of Formula (I) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazale; the class of compounds called the triazoles, such as fluconazole, and itranazole, and the class of compound called the Amphotericins, in particular Amphotericin B and lipsomal Amphotericin B.

The compounds of Formula (I) may also be used for inhibiting and/or reducing the toxicity of an anti-fungal, anti-bacterial or anti-viral agent by administering an effective amount of a compound of Formula (I) to a mammal in need of such treatment. Preferably, a compound of Formula (I) is administered for inhibiting or reducing the toxicity of the Amphotericin class of compounds, in particular Amphotericin B.

The term "$C_{1-3}$ alkyl", "$C_{1-4}$ alkyl", "$C_{1-6}$ alkyl" or "alkyl" groups as used herein is meant to include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like.

"Alkenyl" means both straight or branched chain radicals of 1 to 6 carbon lengths, unless the chain length is limited thereto, including but not limited to vinyl, 1-propenyl, 2-propenyl, or 3-methyl-2-propenyl.

The term "cycloalkyl" or "cycloalkyl alkyl" means groups of 3–7 carbon atoms, such as cyclopropyl, cyclopropylmethyl, cyclopentyl, or cyclohexyl.

"Aryl" or "aralkyl", unless specified otherwise, means an aromatic ring or ring system of 6–10 carbon atoms, such as phenyl, benzyl, phenethyl, or naphthyl. The alkyl chain is meant to include both straight or branched chain radicals of 1 to 4 carbon atoms. "Heteroaryl" means an aromatic ring system containing one or more heteroatoms.

"Halo" means all halogens, i.e., chloro, fluoro, bromo, or iodo.

"Inhibiting the production of IL-1" or "inhibiting the production of TNF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component; and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNP-β are inhibited by the compounds of the present invention and thus are herein referred to collectively as "TNF" unless specifically delineated otherwise. Preferably TNF-α is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferrably, his cytokine is TNF-α.

All of the compounds of Formula (I) are useful in the method of inhibiting the production of TNF, preferably by macrophages, monocytes or macrophages and monocytes, in a mammal, including humans, in need thereof. All of the compounds of Formula (I) are useful in the method of inhibiting or mediating the enzymatic or catalytic activity of PDE IV and in treatment of disease states mediated thereby.

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Preferred compounds are as follows:

When $R_1$ is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) are $CH_2$-cyclopropyl, $CH_2$—$C_{5-6}$ cycloalkyl, $C_{4-6}$ cycloalkyl unsubstituted or substituted with $OHC_{7-11}$ polycycloalkyl, (3- or 4-cyclopentenyl), phenyl, tetrahydrofuran-3-yl, benzyl or $C_{1-2}$ alkyl unsubstituted or substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When $R_1$ term contains the moiety $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH$(—$CH_3$)—, for instance. The individual hydrogen atoms of the repeating methylene unit or the branching hydrocarbon can unsubstituted or be substituted by fluorine independent of each other to yield, for instance, the preferred $R_1$ substitutions, as noted above.

When $R_1$ is a $C_{7-11}$ polycycloalkyl, examples are bicyclo[2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published Nov. 5, 1987.

W is preferably alkyl, alkenyl or alkynyl of 3 to 5 carbon atoms, and where it is alkenyl or alkynyl, that one or two double or triple bonds be present. It is most preferred that W is ethynyl or 1,3-butadiynyl.

Z is preferably $OR_{14}$, $OR_{15}$, $SR_{14}$, $S(O)_m'R_7$, $S(O)_2NR_{10}R_{14}$, $NR_{10}R_{14}$, $NR_{14}C(O)R_9$, $NR_{10}C(O)R_{14}$, $NR_{10}C(O)OR_7$, $NR_{10}C(O)NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$.

Preferred X groups for Formula (I) are dose wherein X is $YR_2$ and Y is oxygen. The preferred $X_2$ group for Formula (I) is that wherein $X_2$ is oxygen. The preferred $X_3$ group for Formula (I) is that wherein $X_3$ is hydrogen. Preferred $R_2$ groups, where applicable, is a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_7$ moieties include unsubstituted or substituted —$(CH_2)_{0-2}$(2-, 3- or 4-pyridyl), $(CH_2)_{1-2}$(2-imidazolyl), $(CH_2)_2$(4-morpholinyl), $(CH_2)_2$(4-piperazinyl) $(CH_2)_{1-2}$(2-thienyl), $(CH_2)_{1-2}$(4-thiazolyl), unsubstituted or substituted pyrimidinyl, and substituted or unsubstituted $(CH_2)_{0-2}$ phenyl.

Preferred rings when $R_{10}$ and $R_{11}$ in the moiety —$NR_{10}R_{11}$ together with the nitrogen to which they are attached form a 5 to 7 membered ring comprised of carbon or carbon and at least one heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazloyl, morpholinyl, piperazinyl, 4-($R_8$)-1-piperazinyl, or pyrrolyl ring.

Preferred rings when $R_{10}$ and $R_{14}$ in the moiety —$NR_{10}R_{14}$ together with the nitrogen to which they are attached may form a 5 to 7 membered ring comprised of carbon or carbon and at least one heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I). Illustrations of such carbon substitutions includes, but is not limited to, 2-($R_7$)-1-imidazolyl, 4-($R_7$)-1-imidazolyl, 5-($R_7$)-1-imidazolyl, 3-($R_7$)-1-pyrazolyl, 4-($R_7$)1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-tetrazolyl. Applicable nitrogen substitution by $R_7$ includes, but is not limited to, 1-($R_7$)-2-tetrazolyl, 2-($R_7$)-1-tetrazolyl, 4-($R_7$)-1-piperazinyl. Where applicable, the ring may be substituted one or more times by $R_7$.

Preferred groups for $NR_{10}R_{14}$ which contain a heterocyclic ring are 5-($R_{14}$)-1-tetrazolyl, 2-($R_{14}$)-1-imidazolyl, 5-($R_{14}$)-2-tetrazolyl, 4-($R_{14}$)-1-piperazinyl, or 4-($R_{15}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl).

When the $R_7$ group is unsubstituted or substituted by a heterocyclic ring such as imidazolyl, pyrazolyl, triazolyl, tetrazolyl, or thiazolyl, the heterocyclic ring itself may be unsubstituted or substituted by $R_8$ on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-($R_8$)-5-pyrazolyl, 1-($R_8$)-4-triazolyl, or 1-($R_8$)-5-triazolyl. Where applicable, the ring may be substituted one or more times by $R_8$.

Preferred are those compounds of Formula (I) wherein $R_1$ is —$CH_2$-cyclopropyl, —$CH_2$—$C_{5-6}$ cycloalkyl, —$C_{4-6}$ cycloalkyl unsubstituted or substituted by OH, tetrahydrofuran-3-yl, (3- or 4-cyclopentenyl), benzyl or —$C_{1-2}$ alkyl unsubstituted or substituted by 1 or more fluorines, and —$(CH_2)_{2-4}OH$; $R_2$ is methyl or fluoro-substituted alkyl, W is ethynyl or 1,3-butadiynyl; $R_3$ is $R_7$ where $R_7$ is an unsubstituted or substituted aryl or heteroaryl ring, X is $YR_2$, and Z is $OR_{14}$, $OR_{15}$, $NR_{10}R_{14}$, or $NR_{14}C(O)R_9$.

Most preferred are those compounds wherein $R_1$ is —$CH_2$-cyclopropyl, cyclopentyl, 3-hydroxycyclopentyl, methyl or $CF_2H$; X is $YR_2$; Y is oxygen; $X_2$ is oxygen; $X_3$ is hydrogen; and $R_2$ is $CF_2H$ or methyl, W is ethynyl or 1,3-butadiynyl, and $R_3$ is a substituted or unsubstituted pyrimidinyl ring.

It will be recognized that some of the compounds of Formula (I) may exist in both racemic and optically active forms; some may also exist in distinct diastereomeric forms possessing distinct physical and biological properties. All of these compounds are considered to be within the scope of the present invention.

Pharmaceutically acceptable salts are prepared in a standard manner. The parent compound, dissolved in a suitable solvent, is treated with an excess of an organic or inorganic acid, in the case of acid addition salts of a base, or an excess of organic or inorganic base where the molecule contains a COOH for example.

Pharmaceutical compositions of the present invention comprise a pharmaceutical carrier or diluent and some amount of a compound of the formula (I). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will, of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to, the skin, eye, ear, or nose.

For parenteral administration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water, for non-aqueous systems, ethanol, glycerin, propylene glycol, corn oil, cottonseed oil, peanut oil, sesame oil, liquid parafins and mixtures thereof with water, for solid systems, lactose, kaolin and mannitol, and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the line, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of formula I is administered to a subject in a composition comprising a nontoxic amount sufficient to produce an inhibition of the symptoms of a disease in which leukotrienes are a factor. Topical formulations will contain between about 0.01 to 5.0% by weight of the active ingredient and will be applied as required as a preventative or curative agent to the affected area. When employed as an oral, or other ingested or injected regimen, the dosage of the composition is selected from the range of from 50 mg to 1000 mg of active ingredient for each administration. For convenience, equal doses will be administered 1 to 5 times daily with the daily dosage regimen being selected from about 50 mg to about 5000 mg.

No unacceptable toxicological effects are expected when these compounds are administered in accordance with the present invention.

Methods Of Preparation

Synthetic Scheme(s) With Textual Description

Compounds of Formula (I) may be prepared by the processes disclosed herein which comprise reacting a terminal acetylene, wherein Z represents Z as defined in relation to Formula (I) or a group convertible to Z, as, e.g., compound 1-Scheme 1, with an appropriate halide, $R_3X$, wherein $R_3$ represents $R_3$ as defined in relation to Formula (I) or a group convertible to $R_3$, in the presence of a suitable catalyst, such as a copper (I) halide and a bivalent or zerovalent palladium compound in the presence of, e.g., triphenylphosphine, in a suitable solvent, such as an amine, as in the pr° Cedure of Brandsma et at. (Syn. Comm., 1990, 20, 1889), provides a compound of the Formula 2-Scheme 1. Compounds of the Formula 1-Scheme 1 may be prepared by pr° Cedures analogous to those described in copending U.S. application 07/862111, 07/968761 and PCT application number PCT/US93/02516 published under WIPO publication number WO93/19751.

Scheme 1

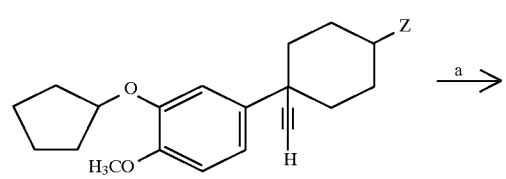

Scheme 1

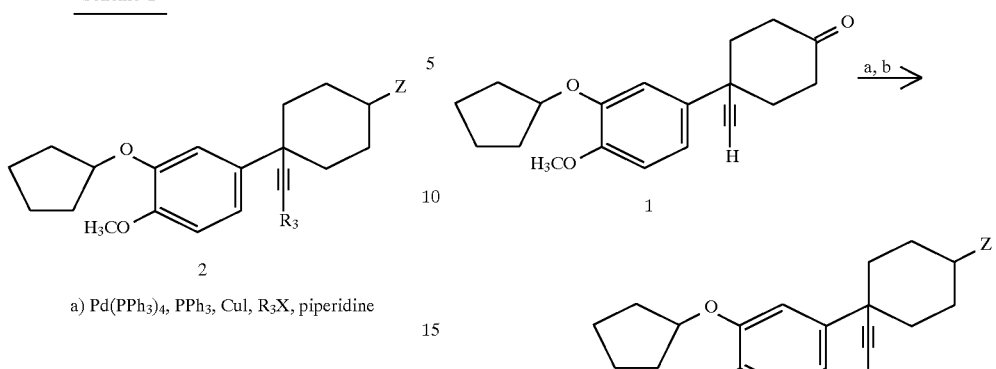

a) Pd(PPh₃)₄, PPh₃, CuI, R₃X, piperidine

Alternatively, compounds of the Formula (I), wherein Z and R₃ represent Z and R₃ as defined in relation to Formula (I) or a group convertible to Z or R₃, may be prepared from the corresponding ketones as, e.g., compound 1-Scheme 2, by the synthetic pr° Cedures described in PCT application number PCT/US93/01990 and PCT/US93/02325 published as WIPO publication number WO93/19750.

Scheme 2

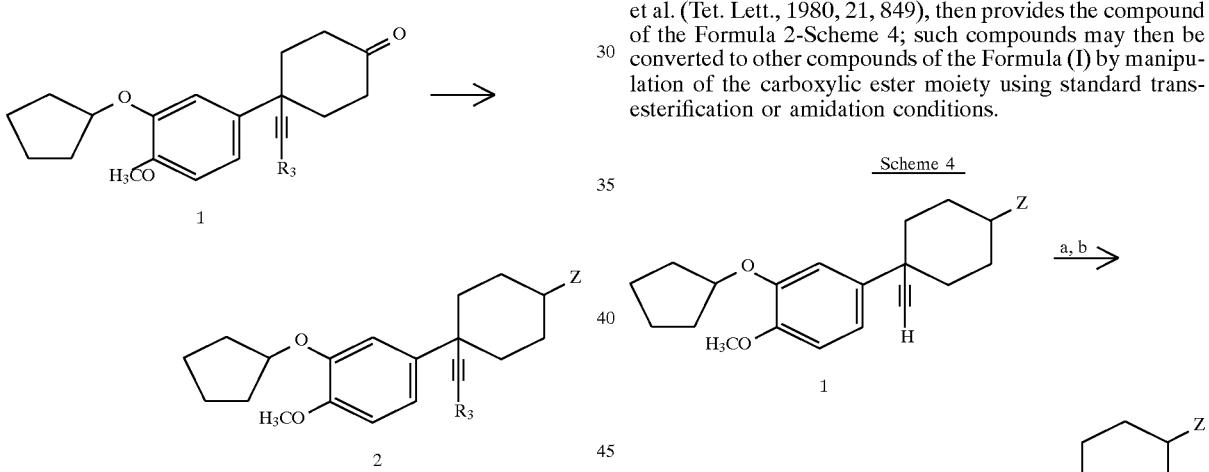

Alternatively, oxidative carbonylation of a terminal acetylene as, e.g., compound 1-Scheme 3, using an appropriate metal salt, such as a copper salt with a catalytic amount of a palladium salt, in the presence of a suitable base as an acid trap, such as sodium acetate, in a suitable alcohol, such as methanol, as in the method of Tsuji et al. (Tet. Lett., 1980, 21, 849), then provides the compound of the Formula 2-Scheme 3; such compounds may then be converted to other compounds of the Formula (I) by manipulation of the ketone as described above and by independent manipulation of the carboxylic ester moiety using standard transesterification or amidation conditions. Syntheses of such ketone starting materials are described in published PCT application PCT/US93/02045 (WIPO publication number WO 93/19748) or published PCT application PCT/US93/02325 (WIPO publication number WO/93/19750).

Scheme 3

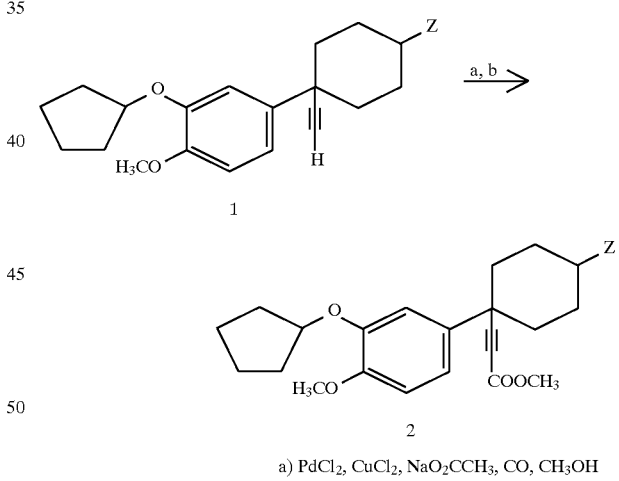

a) PdCl₂, CuCl₂, NaO₂CCH₃, CO, CH₃OH; as inScheme 2

Likewise, oxidative carbonylation of a terminal acetylene as, e.g., compound 1-Scheme 4, wherein Z represents Z as defined in relation to Formula (I) or a group convertible to Z, using an appropriate metal salt, such as a copper salt with a catalytic amount of a palladium salt, in the presence of a suitable base as an acid trap, such as sodium acetate, in a suitable alcohol, such as methanol, as in the method of Tsuji et al. (Tet. Lett., 1980, 21, 849), then provides the compound of the Formula 2-Scheme 4; such compounds may then be converted to other compounds of the Formula (I) by manipulation of the carboxylic ester moiety using standard transesterification or amidation conditions.

Scheme 4 a) PdCl₂, CuCl₂, NaO₂CCH₃, CO, CH₃OH

Compounds where Z is a group other than —OH can be prepared by methods known in the art and in particular by manipulation of the —OH. Such methods are described in co-pending U.S. application Ser. No. 07/968,753 and PCT application Ser. No. PCT/US93/02325 (WIPO publication number WO/93/19750).

Preparation of the remaining compounds of the Formula (I) may be accomplished by procedures analogous to those described above and in the Examples, infra.

It will be recognized that some compounds of the Formula (I) may exist in distinct diastereomeric forms possessing distinct physical and biological properties; such isomers may be separated by standard chromatographic methods.

The following examples are given to further illustrate the described invention. These examples are intented solely for illustrating the invention and should not be read to limit the invention in any manner. Reference is made to the claims for what is reserved to the inventors hereunder.

EXPERIMENTALS

EXAMPLE 1

Preparation of cis-[4-(3-cyclopentyloxy-4-methoxyphenyl)-4-(4-pyridylethynyl) -cyclohexan-1-ol]

1a) trans-[4-(3-cyclopentyloxy-4-methoxyphenyl)4-ethynylcyclohexan-1-ol] and cis-[4-(3-cyclopentyloxy-4-methoxyphenyl)-4-ethynylcyclohexan-1-ol]

To a solution of 4-(3-cyclopentyloxy-4-methoxyphenyl)-4-ethynylcyclohexan-1-one (0.34 g, 1.1 mmol, prepared as described in published PCT application PCT/US93/001990 (WIPO publication number WO 93/19748) or PCT/US93/02325 (WIPO publication number WO/93/19750) in 1,2-dimethoxyethane (5 mL) under an argon atmosphere was added sodium borohydride (0.08 g, 2.2 mmol) and the mixture was stirred at room temperature for 0.5 h. Water was added, the mixture was extracted three times with dichloromethane, was dried (magnesium sulfate) and was evaporated. Purification by flash chromatography, eluting with 3:7 ethyl acetate:hexanes, provided trans-[4-(3-cyclopentyloxy-4-methoxyphenyl)-4-ethynylcyclohexan-1-ol-] (described in U.S. patent application in PCT application number PCT/US93/02516 published under WIPO publication number WO93/1975$_{13}$ as cis-[4-(3-cyclopentyloxy-4-methoxyphenyl)-4-ethynylcyclohexan-1-ol]) as a wax. $^1$H-NMR (400 MHz, CDCl$_3$) δ 7.14 (d, J=2.3 Hz, 1H), 7.04 (dd, J=8.5, 2.3 Hz, 1H), 6.82 (d, J=8.5 Hz, 1H), 4.79 (m, 1H), 3.83 (s, 3H), 3.68 (m, 1H), 2.46 (s, 1H), 1.7–2.1 (m, 14H), 1.6 (m, 2H).

cis-[4-(3-cyclopentyloxy-4-methoxyphenyl)-4-ethynylcyclohexan-1-ol] also was isolated from this pr$^o$Cedure as a colorless oil. $^1$H-NMR (400 MHz, CDCl$_3$) δ 7.17 (d, J=1.9 Hz, 1H), 7.10 (d, J=8.4 Hz, 1H), 6.84 (d, J=8.4 Hz, 1H), 4.80 (m, 1H), 4.13 (br s, 1H), 3.84 (s, 3H), 2.38 (s, 1H), 2.15 (m, 4H), 1.7–2.0 (m, 10H), 1.75 (m, 2H).

1b) cis-[4-(3-cyclopentyloxy-4-methoxyphenyl)-4-(4-pyridylethynyl)cyclohexan-1-ol]

To a solution of trans-[4-(3-cyclopentyloxy-4-methoxyphenyl)4-ethynylcyclohexan-1-ol] (0.15 g, 0.48 mmol) and 4-bromopyridine (0.75 g, 5 mmol) in piperidine (2 mL) under an argon atmosphere were added tetrakis (triphenylphosphine) -palladium(0) (0.022 g, 4%), copper (I) iodide (0.005 g, 6%) and a small crystal of triphenylphosphine, and the mixture was heated at 80°–85° C. for 0.5 h. Ammonium chloride was added and the mixture was extracted three times with dichloromethane, the extract was dried (magnesium sulfate) and was evaporated. Purification by flash chromatography, eluting with 3:1 ethyl acetate/hexanes, provided cis-[4-(3-cyclopentyloxy-4-methoxyphenyl)-4-(4-pyridylethynyl)-cyclohexan-1-ol] as a pale yellow solid, which was triturated from ether-hexanes. mp 183°–184° C. $^1$H-NMR (400 MHz, CDCl$_3$) δ 8.6 (br, 2H), 7.35 (m, 2H), 7.14 (d, J=2 Hz, 1H), 7.06 (dd, J=8.5, 2 Hz, 1H), 6.85 (d, J=8.5 Hz, 1H), 4.79 (m, 1H), 3.85 (s, 3H), 3.7 (m, 1H), 1.8–2.1 (m, 14H), 1.6 (m, 2H).

EXAMPLE 2 cis-[4-(3-cyclopentyloxy-4-methoxyphenyl)-4-(pyrid-2-ylethynyl)cyclohexan-1-ol]

To a solution of trans-[4-(3-cyclopentyloxy-4-methoxyphenyl)-4-ethynyl-cyclohexan-1-ol] (0.14 g, 0.43 mmol) and 2-bromopyridine (0.40 mL, 4.3 mmol) in piperidine (2 mL) under an argon atmosphere were added tetrakis(triphenyl-phosphine)palladium(0) (0.020 g, 4%), copper(I) iodide (0.005 g, 6%) and a small crystal of triphenylphosphine, and the mixture was heated at 80°–85° C. for 0.5 h. Ammonium chloride was added and the mixture was extracted three times with dichloromethane, was dried (magnesium sulfate) and was evaporated. Purification by flash chromatography, eluting with 75:25 ethyl acetate:hexanes, provided cis-[4-(3-cyclopentyloxy-4-methoxyphenyl)-4-(pyrid-2-ylethynyl)cyclohexan-1-ol] as a white solid (0.14 g, 84%), mp 49°–51° C. Anal. (C$_{25}$H$_{29}$NO$_3$.0.5 H$_2$O) calcd: C, 74.97; H, 7.55; N, 3.50; found: C, 74.90; H, 7.52; N, 3.33.

EXAMPLE 3

Resolution of (±)-3-(3-cyclopentyloxy-4-methoxyphenyl)-3-ethynyl-cyclohexan-1one The compound from Example 1b was resolved in the following manner to give enantiomeric oils: HPLC R$_t$=15.5 min (enantiomer 1=E1), 23.2 min (enantiomer 2=E2) (Diacel Chiralpak AS®; 21.2×250 mm; hexane:isopropanol, 4:1; 10 mL/min; UV detection at 295 nm).

EXAMPLE 4

Preparation of (±) 3-(3-cyclopentyloxy-4-methoxyphenyl)3-phenylethynyl-cyclohexan-1-one To a solution of the compound of Example 1b (0.125 g, 0.4 mmol) and iodobenzene (0.4 mL, 2.0 mmol) in piperidine (6 mL) under an argon atmosphere was added trace tetrakis(triphenylphosphine)palladium(0), copper(I) iodide and triphenylphosphine. The mixture was refluxed for 5 h, then concentrated in vacuo. The residue was diluted with ethyl acetate (100 mL), was washed with brine, was dried (MgSO$_4$) and was evaporated. Purification by flash chromatography, eluting with 2:1 hexanes/ethyl acetate, followed by trituration from ether/hexanes, provided the title compound as white solid (0.09 g, 58%), m.p. 90°–91° C.

EXAMPLE 5

Preparation of (±) 3-(3-cyclopentyloxy-4-methoxyphenyl)-3-(3-carbomethoxyphenyl) ethynylcyclohexan-1-one 5a) methyl 3-iodobenzoate Methyl 3-iodobenzoate was prepared by standard chemistry well known to those versed in the art and is a white solid, m.p. 40°–41° C.

5b) (±) 3-(3-cyclopentyloxy-4-methoxyphenyl)3-(3-carbomethoxyphenyl)ethynyl-cyclohexan-1-one To a solution of the compound from Example 1b (0.30 g, 0.96 mmol) and methyl 3-iodobenzoate (0.30 g, 1.15 mmol) in triethylamine (10 mL) under an argon atmosphere was added trace tetrakis(triphenylphosphine)palladium(0), copper(I) iodide and triphenylphosphine. The mixture was refluxed for 0.5 h and was then concentrated in vacuo. The residue was partitioned between water and ethyl acetate. The organic phase was dried (Na$_2$SO$_4$) and was evaporated. Purification by flash chromatography, eluting with 2:1 hexanes/ethyl acetate, provided the title compound as a pale yellow oil (0.35 g, 80%). Anal (C$_{28}$H$_{30}$O$_5$.1.0 H$_2$O) calcd: C, 72.39; H, 6.94; found: C, 72.47; H, 6.80.

EXAMPLE 6

Preparation of (±) 3-(3-carboxyphenylethynyl)-3-(3-cyclopentyloxy-4-methoxyphenyl)cyclohexan-1-one To a solution of the compound from Example 5(b) in 5:5:2 THF/methanol/water (10 mL) under an argon atmosphere was added sodium hydroxide (0.60 g, 1.5 mmol). The mixture was heated at 60° C. for 2 h and was then concentrated in vacuo. The residue was extracted from 3N HCl with ethyl acetate, was washed with brine, was dried ($M_gSO_4$) and was evaporated. Purification by flash chromatography, eluting with 98:2:0.3 chloroform/methanol/acetic acid, provided a white solid, mp. 71°–73° C.

EXAMPLE 7

Preparation of 3-(3-cyclopentyloxy-4-methoxyphenyl)-3[3-(5-methyl-[1.3.4]thiadiazol-2-yl)phenylethynyl]cyclohexan-1-one 7a) 1-iodo-3-(5-methyl-[1,3,4]thiadiazol-2-yl)benzene 1-Iodo-3-(5-methyl-[1,3,4]thiadiazol-2-yl)benzene was prepared by standard chemistry well known to those versed in the art and is white solid, m.p. 86°–89° C. 7b) 3-(3-cyclopentyloxy-4-methoxyphenyl-3-[3-(5-methyl-[1,3,4] thiadiazol-2-yl)phenylethynyl]cyclohexan-1-one To a solution of the compound from Example 3 (E1) (0.10 g, 0.32 mmol) and 1-iodo-3-(5-methyl[1,3,4]thiadiazol-2-yl)benzene (0.10 g, 0.32 mmol) in triethylamine (5 mL) under an argon atmosphere was added trace tetrakis (triphenylphosphine)palladium(0), copper(I) iodide and triphenylphosphine. The mixture was refluxed for 0.20 h, was cooled to room temperature and was concentrated in vacuo. The residue was partitioned between ethyl acetate and water. The organic phase was washed with brine, was dried ($M_gSO_4$) and was evaporated. Purification by flash chromatography, eluting with 1:1 hexanes/ethyl acetate provided the title compound as a white solid (0.135 g, 87%), mp. 97°–99° C.

The enantiomer was prepared in a similar manner, starting with the compound from Example 3 (E2), as a white solid, m.p. 97°–99° C.

EXAMPLE 8

Preparation of 3-(3-cyclopentyloxy-4-methoxyphenyl)-3-[3-(5-methyl-[1,3,4]oxadiazol-2-yl)phenylethynyl]cyclohexan-1-one 8a) 1-Iodo-3-(5-methyl[1,3,4]oxadizol-2-yl)benzene 1-Iodo-3-(5-methyl[1,3,4]oxadiazol-2-yl)benzene was prepared by standard chemistry well known to those versed in the art and is a white solid, m.p. 104°–105° C. 8b) 3-(3-cyclopentyloxy-4-methoxyphenyl)-3-[3-(5-methyl[1,3, 4]oxadiazol-2-yl)phenylethynyl]cyclohexan-1-one To a solution of the compound from Example 3 (0.125 g, 0.4 mmol) and 1-iodo-3-(5-methyl-[1,3,4]oxadiazol-2-yl) benzene (0.09 g, 0.32 mmol) in triethylamine (3 mL) under an argon atmosphere was added trace tetrakis (triphenylphosphine) -palladium(0), copper(I) iodide and triphenylphosphine. The mixture was heated at 80° C. for 0.2 h, was cooled to room temperature and was concentrated in vacuo. The residue was partitioned between ethyl acetate and water. The organic phase was washed with brine, was dried ($M_gSO_4$) and was evaporated. Purification by flash chromatography, eluting with 2:1 ethyl acetate/hexanes, followed by recrystallization from ethyl acetate/hexanes, provided the title compound as a white solid (0.11 g, 61%), m.p. 117°–119° C.

The enantiomer was prepared in a similar manner, starting with the compound from Example 3 (E2), as a white solid, m.p. 117°–119° C.

EXAMPLE 9

Preparation of 3-(3-cyclopentyloxy-4-methoxyphenyl)-3-]3-(3-methyl-[1.2.4]oxadiazol-5-yl)phenylethynyl]cyclohexan-1-one 9a) 1-iodo-3-(3-methyl-[1,2,4]oxadiazol-5-yl)benzene 1-Iodo-3(3-methyl-[1,2,4]oxadiazol-5-yl)benzene was prepared by standard chemistry well known to those versed in the art and is a white solid, m.p. 101.5°–103° C.

9b) 3-(3-cyclopentyloxy-4-methoxyphenyl)-3-[3-(3-methyl-[1,2,4]oxadiazol-5-yl)phenylethynyl]cyclohexan-1-one To a solution of the compound from Example 3 (0.125 g, 0.4 mmol) and 1-iodo-3-(3-methyl-[1,2,4]oxadiazol-5-yl) benzene (0.09 g, 0.32 mmol) in triethylamine (3 mL) under an argon atmosphere was added trace tetrakis (triphenylphosphine)-palladium(0), copper(I) iodide and triphenylphosphine. The mixture was heated at 80° C. for 0.2 h, was cooled to room temperature and was concentrated in vacuo. The residue was partitioned between ethyl acetate and water. The organic phase was washed with brine, was dried ($M_gSO_4$) and was evaporated. The residue was purified by flash chromatography, eluting with 2:1 hexanes/ethyl acetate, followed by trituration from hexanes/ethyl acetate, to provide the title compound as a white solid, m.p. 122°–123° C.

The enantiomer was prepared in a similar manner, starting with the compound from Example 3 (E2), as a white solid, m.p. 122°–123° C.

EXAMPLE 10 preparation of 3-(3-cyclopentyloxy-4-methoxyphenyl)-3-[3-(5-methyl-[1.2.4]oxadiazol-3-yl)phenylethynyl]cyclohexan-1-one 10a) 1-iodo-3-(5-methyl-[1,2,4]oxadiazol-3-yl)benzene 1-iodo-3-(5-methyl-[1,2,4]oxadiazol-3-yl)benzene was prepared by standard chemistry well known to those versed in the art and is a white solid, m.p. 86°–87° C. 10b) 3-(3-cyclopentyloxy-4-methoxyphenyl)-3-[3-(5-methyl-[1, 2,4)oxadiazol-3-yl)phenylethynyl]cyclohexan-1-one To a solution of the compound from Example 3 (0.125 g, 0.4 mmol) and 1-iodo-3-(5-methyl-[1,2,4]oxadiazol-3-yl) benzene (0.09 g, 0.32 mmol) in triethylamine (3 mL) under an argon atmosphere was added trace tetrakis (triphenylphosphine)-palladium(0), copper(I) iodide and triphenylphosphine. The mixture was heated at 80° C. for 0.2 h, was cooled to room temperature and was concentrated in vacuo. The residue was partitioned between ethyl acetate and water. The organic phase was washed with brine, was dried ($M_gSO_4$) and was evaporated. Purification by flash chromatography, eluting with 2:1 hexanes,ethyl acetate, followed by trituration from hexanes/ethyl acetate, provided the title compound as colorless crystals (0.12 g, 67%), m.p. 116°–118° C.

The enantiomer was prepared in a similar manner, starting with the compound from Example 3 (E2), as colorless crystals, m.p.116°–118° C.

EXAMPLE 11

Preparation of 3-(3-cyclopentyloxy-4-methoxyphenyl)-3-(3-cyanophenylethynyl) cyclohexan-1-one To a solution of the compound from Example 3 (E1) (0.125 g, 0.4 mmol) and 3-iodobenzonitrile (Transworld, 0.09 g, 0.4 mmol) in triethylamine (3 mL) under an argon atmosphere was added trace tetrakis(triphenylphosphine) palladium(0), copper(I) iodide and triphenylphosphine. The mixture was heated at 80° C. or 0.2 h, was cooled to room temperature and was concentrated in vacuo. The residue was partitioned between ethyl acetate and water. The organic phase was washed with brine, was dried ($M_gSO_4$) and was evaporated. The residue was purified by flash chromatography, eluting with 2:1 hexanes/ethyl acetate, to provide the title compound as a clear yellow glass (0.12 g, 73%). MS(EI) m/e 414 [M+H]$^+$.

The enantiomer was prepared in similar manner, starting with the compound from Example 3 (E2), as a clear yellow glass.

EXAMPLE 12

Preparation of 3-(3-cyclopentyloxy-4-methoxyphenyl)-3-(3-nitrophenylethynyl) cylcohexan-1-one To a solution of the compound from Example 3 (E1) (0.2 g, 0.64 mmol) and 3-iodonitrobenzene (Aldrich, 0.16 g, 0.64 mmol) in triethylamine (4 mL) under an argon atmosphere was added trace tetrakis(triphenylphosphine)palladium(0), copper(I) iodide and triphenylphosphine. The mixture was heated at 80° C. for 0.2 h, was cooled to room temperature and was concentrated in vacuo. The residue was partitioned between ethyl acetate and water. The organic phase was washed with brine, was dried ($M_gSO_4$) and was evaporated. Purification by flash chromatography, eluting with 3:1 hexanes/ethyl acetate, provided the title compound as yellow solid (0.25 g, 90%), m.p. 46°–48° C.

The enantiomer was prepared in a similar manner, staring with the compound from Example 3 (E2), as a yellow solid. m.p. 46°–48° C.

EXAMPLE 13

Preparation of 3-(3-cyclopentyloxy-4-methoxyphenyl)-3-(2-hydroxyethoxyphenylethynyl) cyclohexan-1-one 13a) 2-hydroxyethoxy-1-iodobenzene 2-hydroxyethoxy-1-iodobenzene was prepared by standard chemistry well known to those versed in the art and is a colorless oil. $^1$H NMR(400 MHz, CDCl$_3$) δ 7.77 (dd, J=7.9, 1.3 Hz, 1H), 7.3 (t, J=7H, 1H), 6.84 (d, J=7.9 Hz, 1H), 6.74 (t, J=7.9 Hz, 1H), 4.13 (t, J=4.3 Hz, 2H), 3.99 (t, J=4.3 Hz, 2H), 2.2 (br s, 1H).

13b) 3-(3-cyclopentyloxy-4-methoxyphenyl)-3 (2-hydroxyethoxyphenylethynyl) -cyclohexan-1-one To a solution of the compound from Example 3 (E1) (0.25 g, 0.8 mmol) and 2-hydroxyethoxy-1-iodobenzene (0.21 g, 0.8 mmol) in triethylamine (5 mL) under an argon atmosphere was added trace tetrakis(triphenylphosphine) palladium(0), copper(I) iodide and triphenylphosphine. The mixture was heated at 80° C. for 1 h, was cooled to room temperature and was concentrated in vacuo. The residue was partitioned between ethyl acetate and water. The organic phase was washed with brine, was dried ($M_gSO_4$) and was evaporated. Purification by flash chromatography, eluting with 1:1 hexanes/ethyl acetate, provided the tide compound as a white solid (0.05 g, 14%), m.p. 93°–94° C.

EXAMPLE 14

Preparation of 3-(3-acetamidophenylethynyl-3-(3-cyclopentyloxy-4-methoxyphenyl)cyclohexan-1-one 14a) 3-acetamido-1-iodobenzene 3-acetamido-1-iodobenzene was prepared by standard chemistry well known to those versed in the art and is a white solid, m.p. 117°–118° C.

14b) 3-(3-acetamidophenylethynyl)-3-(3-cyclopentyloxy-4-methoxyphenyl)cyclohexan-1-one To a solution of the compound from Example 3 (E1) (0.2 g, 0.64 mmol) and 3-acetamido-1-iodobenzene (0.17 g, 0.64 mmol) in triethylamine (5 mL) under an argon atmosphere was added trace tetrakis(triphenylphosphine)palladium(0), copper(I) iodide and triphenylphosphine. The mixture was heated at 80° C. for 0.3 h, was cooled to room temperature and was concentrated in vacuo. The residue was purified by flash chromatography, eluting with 1:1 hexanes/ethyl acetate, to provide the title compound as tan solid (0.17 g, 60%), m.p. 58°–60° C.

EXAMPLE 15

Preparation of 3-(3-cyclopentyloxy-4-methoxyphenyl)-3-(3-methanesulfonamidophenylethynyl)cyclohexan-1-one 15a) 1-iodo-3-methanesulfonamidobenzene 1-iodo-3-methanesulfonamidobenzene was prepared by standard chemistry well known to those versed in the art and is light-pink solid, m.p. 102°–103° C.

15b) 3-(3-cyclopentyloxy-4-methoxyphenyl)-3-(3-methanesulfonamidophenylethynyl)cyclohexan-1-one To a solution of the compound from Example 3 (E1) (0.2 g, 0.64 mmol) and 1-iodo-3-methanesulfonamidobenzene (0.19 g, 0.64 mmol) in triethylamine (5 mL) under an argon atmosphere was added trace tetrakis(triphenylphosphine) palladium(0), copper(I) iodide and triphenylphosphine. The mixture was heated at 80° C. for 0.3 h, was cooled to room temperature and was concentrated in vacuo. The residue was purified by flash chromatography, eluting with 1:1 hexanes/ ethyl acetate, to provide the title compound as a tan solid (0.18 g, 58%), m.p. 59°–62° C.

EXAMPLE 16

Preparation of 3-(3-aminophenylethynyl)-3-(3-cyclopentyloxy-4-methoxyphenyl)cyclohexan-1-one 16a) 1-iodo-3-trifluoroacetamidobenzene 1-iodo-3-trifluoroacetamidobenzene was prepared by standard chemistry well known to those versed in the art and is a white solid, m.p. 120°–121° C.

16b) 3-(3-cyclopentyloxy-4-methoxyphenyl)-3-(3-trifluoroacetamidophenylethynyl) -cyclohexan-1-one To a solution of the compound from Example 3 (E1) (0.5 g, 1.6 mmol) and 1-iodo-3-trifluoroacetamidobenzene (0.5 g, 1.6 mmol) in triethylamine (10 mL) under an argon atmosphere was added a small amount of tetrakis (triphenylphosphine)palladium(0), copper(I) iodide and triphenylphosphine. The mixture was heated at 80° C. for 0.2 h, was cooled to room temperature and was concentrated in vacuo. The residue was purified by flash chromatography, eluting with 3:1 hexane/ethyl acetate, to give the title compound as a pale yellow solid (0.62 g, 78%), m.p. 63°–65° C.

16c) 3-(3-aminophenylethynyl)-3-(3-cyclopentyloxy-4methoxyphenyl)cyclohexan-1-one To a solution of 3-(3-cyclopentyloxy-4- methoxyphenyl) -3-(3-trifluoroacetamidophenylethynyl)cyclohexan-1-one (0.62 g, 1.24 mmol) in 95:5 methanol/water (10 mL) under an argon atmosphere was added potassium carbonate (0.86 g, 6.2 mmol). The mixture was refluxed for 6 h and was stirred for 18 h at room temperature. The solid precipitate was collected and purified by trituration from ethyl acetate/ hexanes to provide the title compound as a white solid (0.39 g, 77%), m.p. 100°–102° C.

EXAMPLE 17 cis-[4-(4-cyanothien-2-ylethynyl)-4-(3-cyclopentyloxy-4-methoxyphenyl) -cyclohexan-1-ol]

17a) 2-bromo-4-cyanothiophene

2-Bromo-5-cyanothiophene was prepared by standard chemistry well known to those versed in the art and is a colorless oil. $^1$H-NMR (400 MHz, CDCl$_3$) δ 7.85 (d, J=2.2 Hz, 1H), 7.25 (d, J=2.2 Hz, 1H) ppm.

17b) cis-[4-(4-cyanothien-2-ylethynyl)-4-(3-cyclopentyloxy-4-methoxyphenyl) -cyclohexan-1-ol]

To a solution of trans-[4-(3-cyclopentyloxy-4-methoxyphenyl)-4ethynyl -cyclohexan-1-ol] (0.20 g, 0.64 mmol) and 2-bromo-4-cyanothiophene (0.12 g, 0.64 mmol) in triethylamine (5 mL) under an argon atmosphere were added tetrakis(triphenyl-phosphine)palladium(0) (0.03 g, 4%), copper(I) iodide (0.008 g, 6%), and a small crystal of triphenylphosphine, and the mixture was heated at 80°–85° C. for 0.5 h. Hydr° Chloric acid (5%) was added and the mixture was extracted three times with dichloromethane, was dried (magnesium sulfate) and was evaporated. Purification by flash chromatography, eluting with 1:1 ethyl acetate:hexanes, followed by trituration from dichloromethane-hexanes, provided cis-[4-(4-cyanothien-2-ylethynyl)-4-(3-cyclopentyloxy-4-methoxyphenyl) cyclohexan-1ol] as a pale yellow solid (0.12 g, 45%), mp 70°–71° C. Anal. (C$_{25}$H$_{27}$NO$_3$S) calcd: C, 71.23; H, 6.46; N, 3.30; found: C, 71.24; H, 6.72; N, 3.14.

EXAMPLE 18 cis-[4-(3-cyclopentyloxy-4-methoxyphenyl)-4-[4-(5-methyl-[1,2,4]oxadiazol-2-yl)thien-2-ylethynyl] cyclohexan-1-ol]

18a) 2-bromo-4-(5-methyl-[1,2,4]oxadiazol-2-yl)thiophene

2-Bromo-4-(5-methyl-[1,2,4]oxadiazol-2-yl)thiophene was prepared by standard chemistry well known to those versed in se art and is a white solid, mp 72°–73° C.

18b) cis-[4-(3-cyclopentyloxy-4-methoxyphenyl)-4-[4-(5-methyl-[1,2,4]oxadiazol-2-yl)thien-2-ylethynyl] cyclohexan-1-ol]

To a solution of trans-[4-(3-cyclopentyloxy-4-methoxyphenyl)-4ethynyl -cyclohexan-1-ol) (0.25 g, 0.8 mmol) and 2-bromo-4-(5-methyl-[1,2,4]oxadiazol-2-yl) thiophene (0.20 g, 0.8 mmol) in triethylamine (5 mL) under an argon atmosphere were added tetrakis (triphenylphosphine)palladium(0) (0.038 g, 4%), copper(I) iodide (0.009 g, 6%) and a small crystal of triphenylphosphine, and the mixture was heated at 70°–75° C. for 0.5 h. Hydrchloric acid (5%) was added and the mixture was extracted three times with dichloromethane, was dried (magnesium sulfate) and was evaporated. Purification by flash chromatography, eluting with 1:1 ethyl acetate:hexanes, provided cis [4-(3-cyclopentyloxy-4-methoxyphenyl)-4-[4-(5methyl-[1,2,4]oxadiazol-2-yl)thien-2-ylethynyl]cyclohexan-1-ol], which was further triturated from dichloromethane-hexanes to give a white solid (0.20 g, 53%), mp 142°–143° C. Anal. (c$_{27}$H$_{30}$N$_2$O$_4$S.0.75 H$_2$O) calcd: C, 65.90; H, 6.45; N, 5.69; found: C, 66.06; H, 6.42; N, 5.50

EXAMPLE 19 cis-[4-(2-aminopyrimidin-4-ylethynyl)-4-(3-cyclopentyloxy-4-methoxyphenyl) -cyclohexan-1ol]

19a) 4-iodo-2-thiomethylpyrimidine

4-Iodo-2-thiomethylpyrimidine was prepared following a literature procedure (A. J. Majeed, Ø. Antonsen, T. Benneche, K. Undheim. *Tetrahedron* 1989, 45, 993–1006).

19b) cis-[4-(3-cyclopentyloxy-4-methoxyphenyl)-4-(2-methylthiopyrimidin-4-ylethynyl) cyclohexan-1-ol]

To a solution of trans-[4-(3-cyclopentyloxy-4-methoxyphenyl)-4-ethynyl -cyclohexan-1-ol] (0.30 g, 0.95 mmol) and 4-iodo-2-thiomethylpyrimidine(0.50 g, 2.5 mmol, as a mixture of 4-iodo-2-thiomethylpyrimidine and 4-chloro-2-thiomethylpyrimidine) in triethylamine (2 mL) udder an argon atmosphere were added tetrakis (triphenylphosphine)palladium(0) (0.044 g, 4%) and copper (I) iodide (0.010 g, 6%), and the mixture was heated at 80°–85° C. for 0.5 h. Ammonium chloride was added and the mixture was extracted three times with dichloromethane, was dried (magnesium sulfate) and was evaporated Purification by flash chromatography, eluting with 1:1 ethyl acetate:hexanes, provided cis-[4-(3-cyclopentyloxy-4 -methoxyphenyl)-4-(2-methylthiopyrimidin-4-ylethynyl) cyclohexan-1-ol] as a yellow oil (0.36 g, 87%). $^1$H-NMR (400 MHz, CDCl$_3$) δ 8.45 (d, J=5.0 Hz, 1H), 7.15 (d, J=2.3 Hz, 1H), 7.03 (dd, J=8.5, 2.3 Hz, 1H), 7.0 1 (d, J=5.0 Hz, 1H), 6.84 (d, J=8.5 Hz, 1H), 4.81 (m, 1H), 3.84 (s, 3H), 3.72 (m, 1H), 2.57 (s, 3H), 2.14 (br d, J=12 Hz, 2H), 2.05 (m, 2H), 1.8–2.0 (m, 10H), 1.6 (m, 2H) ppm.

19c) cis-[4(3-cyclopentyloxy-4-methoxyphenyl)-4-(2-methylsulfonylpyrimidin-4-ylethynyl)cyclohexan-1-ol]

To a solution of cis-[4-(3-cyclopentyloxy-4-methoxyphenyl)-4-(2-methylthiopyrimidin-4-ylethynyl) cyclohexan-1ol] (0.36 g, 0.82 mmol) in chloroform (5 mL) at −10° C. under an argon atmosphere was dropwise added over 20 min. a solution of 3-chloroperoxybenzoic acid (0.34 g, 1.9 mmol) in chloroform (3 mL). The reaction was stirred 3 h at −10° C., then 3 h at room temperature. A second portion of 3-chloroperoxybenzoic acid (0.11 g, 0.62 mmol) in chloroform (1 mL) was added and stirring was continued for 1.5 h. The reaction was quenched with sodium carbonate (5%), was extracted three times with dichloromethane, was dried (potassium carbonate) and was evaporated Purification by flash chromatography, eluting with 2.5:97.5 methanol:dichloromethane, provided cis-[4-(3-cyclopentyloxy-4-methoxyphenyl)-4-(2-methylsulfonylpyrimidin-4-ylethynyl)cyclohexan-1-ol] as a white foam (0.31 g, 81%), mp 75°–77° C. $^1$H-NMR (400 MHz, CDCl$_3$) δ 8.84 (d, J=5.3 Hz, 1H), 7.54 (d, J=5.3 Hz, 1H), 7.10 (d, J=2.3 Hz, 1H ) 7.04 (dd, J=8.5, 2.3 Hz, 1H), 6.85 (d, J=8.5 Hz, 1H), 4.81 (m, 1H), 3.85 (s, 3H), 3.73 (m, 1H), 3.38 (s, 3H), 2.20 (br d, J=12 Hz, 2H), 2.06 (m, 2H), 1.8–2.0 (m, 10H), 1.6 (m, 2H) ppm.

19d) cis-[4-(2-aminopyrimidin-4-ylethynyl)-4-(3-cyclopentyloxy-4-methoxyphenyl) -cyclohexan-1-ol]

Into a solution of cis-[4-(3-cyclopentyloxy-4-methoxyphenyl)-4-(2-methylsulfonylpyrimidin-4-ylethynyl) cyclohexan-1-ol] (0.31 g, 0.66 mmol) in methanol (5 mL) at −78° C. was condensed liquid ammonia (5 ml). The pressure tube was sealed and the reaction was stirred at room temperature for 2 h. After cooling, the solvents were evaporated Purification by flash chromatography, eluting with 4:96 methanol:dichloromethane, followed by trituration from dichloromethane-ether-hexanes, provided cis-[4-(2-aminopyrimidin-4-ylethynyl)-4-(3-cyclopentyloxy-4-methoxyphenyl)cyclohexan-1-ol] as a white solid (0.19 g, 74%), mp 173°–174° C. Anal. (C$_{24}$H$_{29}$N$_3$O$_3$.0.25 H$_2$O) calcd: C, 69.96; H, 7.22; N, 10.20; found: C, 69.66; H, 7.10; N, 10.11.

EXAMPLE 20 cis-[4-(2- aminopyrimidin-5-ylethynyl)-4-(3-cyclopentyloxy-4-methoxyphenyl) -cyclohexan-1-ol]

To a solution of trans-[4-(3-cyclopentyloxy-4-methoxyphenyl)-4-methoxyphenyl)-4-ethynyl -cyclohexan-1-ol] (0.20 g, 0.64 mmol) and 2-amino-5-bromopyrimidine (0.55 g, 3.2 mmol) in piperidine (2 mL) under an argon atmosphere were added tetrakis(triphenyl-phosphine) palladium(0) (0.030 g, 4%), copper(I) iodide (0.006 g, 6%) and a small crystal of triphenylphosphine, and the mixture was heated at 80°–85° C. for 0.5 h. Water was added and the mixture was extracted three times with dichloromethane, was dried (potassium carbonate) and was evaporated. Purification by two successive flash chromatographies, eluding first with 5:95 methanol:dichloromethane, then with 3:97 methanol:dichloromethane, provided cis-[4-(3-cyclopentyloxy-4-methoxyphenyl)-4-(2-aminopyrimidin-5-ylethynyl) cyclohexan-1-ol] as a tan-brown solid (0.076 g, 29%), mp 136°–137° C. Anal. ($C_{24}H_{29}N_3O_3$. 0.75 $H_2O$) calcd: C, 68.47; H, 7.30; N, 9.98; found: C, 68.25; H, 7.09; N, 9.78.

EXAMPLE 21 cis-[4-(thiazol-2-ylethynyl)-4-(3-cyclopentyloxy-4-methoxyphenyl)cyclohexan-1ol]

To a solution of trans-[4-(3-cyclopentyloxy-4-methoxyphenyl)-4-ethynyl -cyclohexan-1-ol] (0.15 g, 0.48 mmol) and 2-bromothiazole (0.20 mL, 2.4 mmol) in triethylamine (1.5 mL) under an argon atmosphere were added tetrakis(triphenyl phosphine)palladium(0) (0.022 g, 4%), copper(I) iodide (0.006 g, 6%) and a small crystal of triphenylphosphine, and the mixture was heated at 80°–85° C. for 1 h. Ammonium chloride was added and the mixture was extracted three times with dichloromethane, dried (magnesium sulfate), and evaporated. Purification by two successive flash chromatographies, eluting first with 6:4 ethyl acetate:hexanes, then with 2:98 methanol:dichloromethane, provided cis-[4-(3-cyclopentyloxy-4-methoxyphenyl)-4-(2-aminopyrimidin-5-ylethynyl)cyclohexan-1-ol] as an off-white foam (0.13 g, 68%), mp 45°–48° C. Anal. ($C_{23}H_{27}NO_3S.0.5\ H_2O$) calcd: C, 67.95; H, 6.94; N, 3.45; found: C, 67.91; H, 6.76; N, 3.39.

EXAMPLE 22 trans-[4-(3-cyclopentyloxy-4-methoxyphenyl)-4-(pyrid-2-ylethynyl)cyclohexyl-1-amine]

22a) cis-[4-(3-cyclopentyloxy-4-methoxyphenyl)-4-ethynylcyclohexyl-1-amine]

To a solution of trans-[4-(3-cyclopentyloxy-4-methoxyphenyl)-4-ethynyl -cyclohexan-1-ol] (1.0 g, 3.18 mmol), phthalimide (0.70 g, 4.77 mmol) and triphenylphosphine (1.25 g, 4.77 mmol) in tetrahydrofuran (32 mL) was dropwise added diethyl azodicarboxylate (0.75 mL, 4.77 mmol), and the solution was stirred under an argon atmosphere at room temperature for 2 h. Evaporation and purification by flash chromatography, eluting with 2:8 ethyl acetate hexanes, provided the intermediate phthalimide (1.43 g) as a waxy white solid, mp 45°–52° C. This was dissolved in 2:1 ethanol:tetrahydrofuran (30 mL), was treated with hydrazine hydrate (1.55 mL, 32 mmol) and was stirred under an argon atmosphere at room temperature for 4 days. Water was added and the mixture was extracted three times with 10:90 methanol:dichloromethane, was dried (potassium carbonate) and was evaporated. Purification by flash chromatography, eluting with 0.5:5:95 ammonium hydroxide:methanol:dichloromethane, provided cis-[4-(3-cyclopentyloxy4-methoxyphenyl)-4-ethynyl-cyclohexyl-1-amine] as a colorless oil (0.71 g, 72%). $^1$H-NMR (400 MHz, $CDCl_3$) δ 7.17 (d, J=2.2 Hz, 1H), 7.09 (dd, J=8.5, 2.2 Hz, 1H), 6.82 (d, J=8.5 Hz, 1H), 4.81 (m, 1H), 3.82 (s, 3H), 3.26 (br s, 1H), 2.36 (br s, 1H), 2.1–2.2 (m, 4H), 1.8–2.0 (m, 10H), 1.6, (m, 2H) ppm.

22b) cis-[1-tert-butoxycarbonylamino-4-(3-cyclopentyloxy-4-methoxyphenyl4-ethynylcyclohexane]

A mixture of cis-[4(3-cyclopentyloxy-4-methoxyphenyl)-4-ethynylcyclohexyl -1-amine] (0.55 g, 1.75 mmol) and di-tert-butyldicarbonate (0.42 g, 1.93 mmol) in dichloromethane (8 mL) was stirred 20 h and was evaporated. Purification by flash chromatography, eluting with 2:8 ethyl acetate:hexanes provided, cis-[1-tert-butoxycarbonylamino-4-(3-cyclopentyloxy-4-methoxyphenyl)-4-ethynylcyclohexane] as a colorless oil (0.70 g, 97%). $^1$H-NMR (400 MHz, $CDCl_3$) δ 7.13 (d, J=2.2 Hz, 1H), 7.02 (dd, J=8.5, 2.2 Hz, 1H), 6.84 (d, J=8.5 Hz, 1H), 4.81 (m, 1H), 4.64 (m, 1H),3.84 (s, 3H), 2.36 (s, 1H), 2.05 (m, 2H), 1.6–2.0 (m, 14H), 1.45, (s, 9H) ppm.

22c) trans-[1-tert-butoxycarbonylamino-4-(3-cyclopentyloxy-4-methoxyphenyl)-4-(pyrid2-ylethynyl-cyclohexane]

To a solution of cis -[1-tert-butoxycarbonylamino-4-(3-cyclopentyloxy-4-methoxyphenyl)-4-ethynylcyclohexane] (0.35 g, 0.85 mmol) and 2-bromopyridine (0.80 mL, 8.5 mmol) in piperidine (2.5 mL) under an argon atmosphere were added tetrakis(triphenylphosphine)palladium(0) (0.039 g, 4%), copper(I) iodide (0.010 g, 6%) and a small crystal of triphenylphosphine, and the mixture was heated at 80°–85° C. for 0.5 h in the dark. Water was added and the mixture was extracted three times with dichloromethane, was dried (magnesium sulfate) and was evaporated. Purification by flash chromatography, eluting with 25:75 ethyl acetate:hexanes, provided trans-[1-tert-butoxycarbonylamino-4-(3-cyclopentyloxy-4-methoxyphenyl)-4-(pyrid-2-ylethynylcyclohexane] as a light yellow solid (0.30 g, 72%), mp 69°–70° C. $^1$H-NMR (400 MHz, $CDCl_3$) δ 8.57 (d, J=4 Hz, 1H), 7.66 (dt, J=8, 4 Hz, 1H), 7.42 (d, J=8 Hz, 1H), 7.26 (br, 1H), 7.17 (d, J=2.2 Hz, 1H), 7.09 (dd, J=8.5, 2.2 Hz, 1H), 6.85 (d, J=8.5 Hz, 1H), 4.82 (m, 1H), 4.64 (br s, 1H), 3.25 (s, 3H), 2.2 (m, 2H), 1.8–2.1 (m, 12H), 1.6 (m, 2H),1.45, (s, 9H) ppm.

22d) trans-[4-(3-cyclopentyloxy-4-methoxyphenyl)-4-(pyrid-2-ylethynyl)cyclohexy-1-amine]

To a solution of trans-[1-tert-butoxycarbonylamino-4-(3-cyclopentyloxy-4-methoxyphenyl)-4-(pyrid-2-ylethynylcyclohexane] (0.30 g, 0.61 mmol) in dichloromethane (5 mL) at 0° C. under an argon atmosphere was added trifluoroacetic acid (0.60 mL, 7.89 mmol). The reaction was stirred at room temperature for 6 h, was cooled to 0° C., quenched with sodium bicarbonate, was diluted with water, was extracted with three times dichloromethane, was dried (magnesium sulfate) and was evaporated. Purification by flash chromatography, eluting with 0.7:7:93 ammonium hydroxide:methanol:dichloromethane provided trans-[4-(3-cyclopentyloxy-4-methoxyphenyl)-4-(pyrid-2-ylethynyl) cyclohexyl-1-amine] as a very viscous oil (0.19 g, 82%). $^1$H-NMR (400 MHz, $CDCl_3$) δ 8.59 (d; J=4 Hz, 1H), 7.63 (dt, J=7.8, 4 Hz, 1H), 7.41 (d, J=7.8 Hz, 1H), 7.26 (m, 1H), 7.22 (m, 2H), 6.81 (d, J=8.5 Hz, 1H), 4.84 (m, 1H), 3.81 (s, 3H), 3.4 (br s, 1H), 2.31 (m, 4H), 1.8–2.0 (m, 10H), 1.6 (m, 2H) ppm. Anal. ($C_{25}H_{30}N_2O_2.0.5\ H_2O$) calcd: C, 75.16; H, 7.82; N, 7.01; found: C, 75.42; H, 7.77; N, 6.91.

EXAMPLE 23 trans-[4-(3-cyclopentyloxy-4-methoxyphenyl)-4-(pyrid-2-ylethynyl)cyclohexyl-1-formamide]

To a preparation of acetic formic anhydride (0.035 mL, 0.38 mmol) at 0° C. under an argon atmosphere was added a solution of trans-[4-(3-cyclopentyloxy-4-methoxyphenyl)-4-(pyrid-2-ylenthynyl)cyclohexyl-1-amine] (0.096 g, 0.24 mmol) in tetrahydrofuran (1.5 mL). The mixture was stirred for 3 h at room temperature, was diluted with dichloromethane, was washed with sodium bicarbonate and water, was dried (magnesium sulfate) and was evaporated. Purification by flash chromatograhy, eluting with 5:95 methanol:dichloromethane, provided trans-[4-(3-cyclopentyloxy-4-methoxyphenyl)-4-(pyrid-2-ylethynyl) cyclohexyl-1-formamide] (which contains a trace of acetamide) as a white foam (0.08 g, 79%), mp 75°–76° C. Anal. ($C_{26}H_{30}N_2O_3 \cdot 0.375\ H_2O$) calcd: C, 73.43; H, 7.26; N, 6.59; found: C, 73.46; H, 7.29; N, 6.25.

EXAMPLE 24 trans-[4-(3-cyclopentyloxy-4-methoxyphenyl)-4-[5-(5-methyl-[1,2,4]oxadiazol-2-yl)thien-2-ylethynyl] cyclohexyl-1-amine], cyclohexylsulfamate salt 24a) 2-bromo-5-(5-methyl-[1,2,4]oxadiazol-2-yl)thiophene 2-Bromo-5-(5-methyl-[1,2,4]oxadiazol-2-yl)thiophene was prepared by standard chemistry well known to those versed in the art and was a white solid, mp 48°–49° C.

24b) trans-[1-tert-butoxycarbonylamino-4-(3-cyclopentyloxy-4-methoxyphenyl)-4-[5-(5-methyl-[1,2,4] oxadiazol-2-yl)thien-2-ylethynyl]cyclohexane]

To a solution of cis-[1-tert-butoxycarbonylamino-4-(3-cyclopentyloxy-4-methoxyphenyl)-4-ethynylcyclohexane] (0.30 g, 0.73 mmol) and 2-bromo-5-(5-methyl -[1,2,4] oxadiazol-2-yl)thiophene (0.18 g, 0.73 mmol) in triethylamine (5 mL) under an argon atmosphere were added tetrakis(triphenylphosphine)palladium(0) (0.033 g, 4%) and copper(I) iodide (0.008 g, 6%) and a small crystal of triphenylphosphine, and the mixture was heated at 80°–85° C. for 1 h. Water was added and the mixture was extracted three times with dichloromethane, was dried (magnesium sulfate) and was evaporated. Purification by flash chromatography, eluting with 2:8 ethyl acetate:hexanes, followed by trituration from dichloromethane-hexanes, provided trans-[1-tert-butoxycarbonylamino-4-(3-cyclopentyloxy-4-methoxyphenyl)-4-[5-(5-methyl-[1,2,4] oxadiazol-2-yl)thien-2-ylethynyl]cyclohexane] as a yellow foam (0.38 g), containing ~40% of 1,4-bis-{[t-4-(3-cyclopentyloxy-4-methoxyphenyl)-r-1-cyclohexyl-1-amine]-4-yl}buta-1,3-diyne by $^1$H-NMR.

24c) trans-[4-(3-cyclopentyloxy-4-methoxyphenyl)-4-[5-(5-methyl-[1,2,4]-oxadiazol-2-yl)thien-2-ylethynyl] cyclohexyl-1-amine], cyclohexylsulfamate salt A solution of trans-[1-tert-butoxycarbonylamino-4-(3-cyclopentyloxy-4-methoxyphenyl)-4-[5-(5-methyl-[1,2,4] oxadiazol-2-yl)thien-2-ylethynyl] cyclohexane] (0.38 g, containing 40% of the dimer) in dichloromethane (10 mL) at 0° C. under an argon atmosphere was treated with trifluoroacetic acid (0.50 mL, 6.5 mmol) and the mixture was stirred for 24 h at room temperature. The solution was quenched with sodium bicarbonate at 0° C., was diluted with water, was extracted three times with 10:90 methanol:dichloromethane, was dried (potassium carbonate) and was evaporated. Purification by flash chromatography, eluting with 0.5:5:95 ammonium hydroxide:methanol:dichloromethane, provided trans-[4-(3-cyclopentyloxy-4-methoxyphenyl)-4-[5-(5-methyl-[1,2,4] oxadiazol-2-yl)thien-2-ylethynyl]cyclohexyl-1-amine] as a glassy solid (0.18 g, 59%). This was dissolved in acetone (0.5 mL) and added to a solution of cyclohexylsulfamic acid (0.066 g, 0.37 mmol) in acetone (0.5 mL). The salt was isolated and the free amine was recovered. A second chromatography using the same solvent system provided free amine (0.048 g), which was treated with cyclohexylsulfamic acid (0.018 g, 0.10 mmol) in acetone (1 mL). After the addition of ether (20 mL), the precipitate was filtered off to provide trans-[4-(3-cyclopentyloxy-4-methoxyphenyl)-4-[5-(5-methyl-[1,2,4]oxadiazol-2-yl)thien-2-ylethynyl] cyclohexyl-1-amine], cyclohexylsulfamate salt (0.043 g, 18%) as a white solid, mp 134°–135° C. Anal. ($C_{33}H_{44}N_4O_6S_2 \cdot 0.5\ H_2O$) calcd: C, 59.52; H, 6.81; N, 8.41; found: C, 59.37; H. 6.71; N, 8.46.

EXAMPLE 25 cis-[4-(3-cyclopentyloxy-4-methoxyphenyl)-4-(pyrid-2-ylethynyl)cyclohexyl-1-amine]

25a) cis-[1-tert-butoxycarbonylamino-4-(3-cyclopentyloxy-4-methoxyphenyl)4-ethynyl-cyclohexane]

A solution of 4-(3-cyclopentyloxy-4-methoxyphenyl)-4-ethynyl-cyclohexan-1-one (0.82 g, 2.63 mmol), ammonium acetate (2.03 g, 26 mmol), sodium cyanoborohydride (0.17 g, 2.63 mmol) and several 4 Å molecular sieves in methanol (10 mL) was stirred under an argon atmosphere at room temperature for 3 days. Several crystals of methyl orange were added, then hydrogen chloride-saturated methanol to ~pH 3. The reaction was made basic with sodium hydroxide (10%), was extracted with 10:90 methanol:dichloromethane, was dried (potassium carbonate) and was evaporated to provide crude trans-[4-(3-cyclopentyloxy-4-methoxyphenyl)4-ethynylcyclohexyl-1-amine] as a yellow oil (0.88 g, 100%). A solution of the intermediate in dichloromethane (15 mL) was treated with di-tert.-butyldicarbonate (0.63 g, 2.89 mmol), was stained 5 h and was evaporated. Purification by flash chromatography, eluting with 15:85 ethyl acetate:hexanes, provided trans-[1-tert-butoxycarbonylamino-4-(3-cyclopentyloxy-4-ethoxyphenyl)4-ethynylcyclohexane] as a white foam (0.57 g, 53%, $^1$H-NMR shows ~20% cis isomer), mp.39°–43° C. $^1$H-NMR (400 MHz, CDCl$_3$) δ 7.11 (d, J=2.2 Hz, 1H), 7.04 (dd, J=8.5, 2.2 Hz, 1H), 682 (d, J=8.5 Hz, 1H), 4.80 (m, 1H), 4.6 (m, 0.2H), 4.5 (m, 0.8H), 4.0 (m, 0.2H), 3.84 (s, 0.6H), 3.83 (s, 2.4H), 2.43 (s, 0.8H), 2.36 (s, 0.2H), 1.6–2.1 (m, 16H), 1,46, (s, 9H) ppm.

25b) cis-[1-tert-butoxycarbonylamino-4-(3-cyclopentyloxy-4-methoxyphenyl-4-(pyrid-2-ylethynylcyclohexane To a solution of trans-[1-tert-butoxycarbonylamino-4-(3-cyclopentyloxy-4-methoxyphenyl)-4-ethynylcyclohexane] (0.45 g, 1.09 mmol) and 2-bromopyridine (1.0 mL, 11 mmol) in piperidine (3 mL) under an argon atmosphere were added tetrakis(triphenylphosphine)palladium(0) (0.050 g, 4%), copper(I) iodide (0.012 g, 6%) and a small crystal of triphenylphosphine, and the mixture was heated at 80°–85° C. for 0.5 h in the dark. Water was added and the mixture was extracted three times with dichloromethane, was dried (magnesium sulfate) and was evaporated. Purification by flash chromatography, eluting with 2:8 ethyl acetate:hexanes, provided cis-[1-tert -butoxycarbonylamino-4-(3-cyclopentyloxy-4-methoxyphenyl)4-(pyrid-2 -ylethynylcyclohexane] as a yellow foam (0.41 g, 78%, contains ~35% trans isomer by $^1$H-NMR), mp 40°–43° C. $^1$H-NMR (400 MHz, CDCl$_3$) δ 8.4 (m, 1H), 7.65 (m, 1H), 7.4 (d, 1H), 7.1 (m, 3H), 6.85 (m, 1H), 4.8 (m, 1H), 4.6 (m, 0.65H), 3.85 (s, 1H), 3.84 (s, 2H), 3.55 (m. 0.65H), 1.5–2.2 (m, 16H), 1.45, (s, 9H) ppm.

25c) cis-[4-(3-cyclopentyloxy-4-methoxyphenyl)-4-(pyrid-2-ylethynyl)cyclohexyl-1-amine]

To a solution of cis-[1-tert-butoxycarbonylamino-4-(3-cyclopentyloxy-4-methoxyphenyl-4-(pyrid-2-ylethynylcyclohexane] (0.41 g, 0.84 mmol) in dichloromethane (5 mL) at 0° C. under an argon atmosphere was added trifluoroacetic acid (0.65 mL, 8.4 mmol). The reaction was stirred at room temperature for 20 h, was cooled to 0° C., was quenched with sodium bicarbonate, was diluted with water, was extracted twice with 10:90 methanol:dichloromethane, was dried (potassium carbonate) and was evaporated. Purification by flash chromatography, eluting with 0.5:5:95 ammonium hydroxide:methanol:dichloromethane, followed by trituration from ether, provided cis-[4-(3-cyclopentyloxy-4-methoxyphenyl)-4-(pyrid-2-ylethynyl)cyclohexyl-1-amine] as a white solid (0.23 g, 69%, containing ~20% of the trans isomer), mp 78°–80° C. Anal. ($C_{25}H_{30}N_2O_2$) calcd: C, 66.06; H, 6.65; N, 6.16; found: C, 65.73; H, 6.96; N, 5.98.

EXAMPLE 26 cis-[4-(3-cyclopentyloxy-4-methoxyphenyl)-4-(pyrid-2-ylethynyl)cyclohexyl-1-formamide]

To a preparation of acetic formic anhydride (0.057 mL, 0.64 mmol) at 0° C. under an argon atmosphere was added a solution of cis-[4-(3-cyclopentyloxy-4-methoxyphenyl)-4-(pyrid-2-ylethynyl)cyclohexyl-1-amine] (0.16 g, 0.40 mmol) in tetrahydrofuran (1.5 mL). The mixture was stirred for 3 h at room temperature, was diluted with dichloromethane, was washed with sodium bicarbonate and water, was dried (magnesium sulfate) and was evaporated Purification by flash chromatograhy, eluting with 5:95 methanol:dichloromethane, provided cis-[4-(3-cyclopentyloxy-4-methoxyphenyl)-4-(pyrid-2-ylethynyl)cyclohexy-1-formamide] (which contains a trace of acetamide) as a white foam (0.08 g, 79%), mp 80°–81° C. Anal. ($C_{26}H_{30}N_2O_3 \cdot 0.375\ H_2O$) calcd: C, 73.3; H, 7.26; N, 6.59; found: C, 73.46; H, 7.29; N, 6.25.

EXAMPLE 27 cis-[4-(3-cyclopentyloxy-4-methoxyphenyl)-4-[5-(5-methyl-[1,2,4]oxadiazol-2-yl)thien-2-ylethynyl]cyclohexyl-1-amine],cyclohexylsulfamate salt 27a) 2-bromo-5-(5-methyl-[1,2,4]oxadiazol-2-yl)thiophene 2-Bromo-5-(5-methyl-[1,2,4]oxadiazol-2-yl)thiophene was prepared by standard chemistry well known to those versed in the art and is a white solid, mp 48°–49° C.

27b) cis-[1-tert-butoxycarbonylamino-4-(3-cyclopentyloxy-4-methoxyphenyl)-4-[5-(5-methyl-[1,2,4]oxadiazol-2-yl)thien-2-ylethynyl]cyclohexane]

To a solution of trans-[4-(3-cyclopentyloxy-4-methoxyphenyl)-4-ethynyl-cyclohexyl-1-amine] (0.21 g, 0.52 mmol) and 2- bromo-5-(5-methyl-[1,2,4]oxadiazol-2-yl)thiophene (0.13 g, 0.52 mmol) in triethylamine (5 mL) under an argon atmosphere were added tetrakis(triphenylphosphine)palladium(0) (0.024 g, 4%), copper(I) iodide (0.006 g, 6%) and a small crystal of triphenylphosphine, and the mixture was heated at 80°–85° C. for 1 h. Ammonium chloride was added and the mixture was extracted three times with dichloromethane, was dried (magnesium sulfate) and was evaporated. Purification by two successive flash chromatographies, eluting first with 2:8 ethyl acetate:hexanes, then with 2:8 acetone:hexanes, provided cis-[1-tert-butoxycarbonylamino-4-(3-cyclopentyloxy-4-methoxyphenyl)-4-[5-(5-methyl-[1,2,4] oxadiazol-2-yl)thien-2-ylethynyl]cyclohexane] as a white foam (0.20 g, 69%, contains ~20% dimer impurity by $^1$H-NMR), mp 60°–68° C.

27c) cis-[4-(3-cyclopentyloxy-4-methoxyphenyl)-4-[5-(5-methyl-[1,2,4]oxadiazol-2-yl)thien-2-ylethynyl]cyclohexyl-1-amine], cyclohexylsulfamate salt A solution of cis-[1-tert-butoxycarbonylamino-4-(3-cyclopentyloxy-4-methoxyphenyl)-4-[5-(5-methyl-[1,2,4] oxadiazol-2-yl)thien-2-ylethynyl]cyclohexane] (0.21 g, containing 20% of the dimer) in dichloromethane (5 mL) at 0° C. under an argon atmosphere was treated with trifluoroacetic acid (0.28 mL, 3.6 mmol) and was stirred 24 h at room temperature. The solution was quenched with sodium bicarbonate at 0° C., was diluted with water, was extracted three times with 10:90 methanol:dichloromethane, was dried (potassium carbonate) and was evaporated. Purification by flash chromatography, eluting with 1.3:3:97 ammonium hydroxide:methanol:dichloromethane, provided cis-[4-(3-cyclopentyloxy-4-methoxyphenyl-4-[5-(5-methyl-[1,2,4] oxadiazol-2-yl)thien-2-ylethynyl]cyclohexyl-1-amine] as a colorless glass (0.11 g, 0.24 mmol, 69%). This intermediate was dissolved in acetone (0.5 mL) and was added to a solution of cyclohexylsulfamic acid (0.045 g, 0.24 mmol) in acetone (1 mL). After the addition of ether, the precipitate was filtered off to provide cis-[4-(3-cyclopentyloxy-4-methoxyhenyl)-4-[5-(5-methyl -[1,2,4]oxadiazol-2-yl)thien-2-ylethynyl]cyclohexyl-1-amine], cyclohexylsulfamate salt (0.14 g, 58%) as a white solid, mp 152°–154° C. Anal. ($C_{33}H_{44}N_4O_6S_2$) calcd: C, 60.34; H, 6.75; N, 8.53; found: C, 60.01; H, 6.63; N, 8.32.

EXAMPLE 28 cis-[4-(3-cyclopentyloxy-4-methoxyphenyl)-4-(2-[3-(3-methyl[1,2,4,]oxadiazol-5-yl)phenyl]ethynyl)cyclohexan-1-ol], 28a) 5-(3-iodophenyl)-3-methyl[1,2,4]oxadiazole 5-(3-Iodophenyl)-3-methyl[1,2,4]oxadiazole was prepared by standard chemistry well known to those versed in the art and was a white solid, mp 102°–103° C.

28b) cis-[4-(3-cyclopentyloxy-4-methoxyphenyl)-4-(2-[3-(3-methyl[1,2,4]oxadiazol-5-yl)phenyl]ethynyl)cyclohexan-1-ol]

To a solution of trans-[4-(3-cyclopentyloxy-4-methoxyphenyl)-4-ethynyl-cyclohexan-1-ol] (0.11 g, 0.35 mmol) and 5-(3-iodophenyl)3-methyl(1,2,4]oxadiazole (0.15 g, 0.52 mmol) in triethylamine (4 mL) under an argon atmosphere were added tetrakis(triphenylphosphine) palladium (0.017 g, 0.015 mmol), copper(I) iodide (0.004 g, 0.021 mmol) and a small crystal of triphenylphosphine. After heating the mixture at 70° C. for 1.5 h., the reaction was quenched by addition of aqueous ammonium chloride solution, and the solvent was concentrated. The mixture was extracted three times with methylene chloride, and the organic phase was washed with water, was dried (sodium sulfate) and was evaporated. Purification by flash chromatography, eluting with 45:55 ethyl acetate:hexanes and crystallizing from ethyl ether, provided cis-[4-(3-cyclopentyloxy-4-methoxyphenyl)-4-(2-[3-(3-methyl[1,2,4] oxadiazol-5-yl)phenyl]ethynyl)cyclohexan-1-ol] as a white solid (0.144 g, 87%), mp 71.5°–73.5° C. Anal. ($C_{29}H_{32}N_2O_4$) calcd: C, 73.71; H, 6.83, N, 5.93 found: C, 73.60; H, 6.91, N, 5.76.

EXAMPLE 29 cis-[4-(3-cyclopentyloxy-4-methoxyphenyl)-4-(2-[3-(5-methyl[1,3,4]oxadiazol-2-yl)phenyl]ethynyl) cylcohexan-1-ol]

29a) 2-(3-iodophenyl)-5-methyl(1,3,4)oxadiazole 2-(3-Iodophenyl)-5-methyl[1,3,4]oxadiazole was prepared by standard chemistry well known to those versed in the art and is a white solid, mp 112°–113.5° C.

29b) cis-[4-(3-cyclopentyloxy-4-methoxyphenyl)-4-(2-[3-(5-methyl[1,3,4]oxadiazol -2-yl)phenyl]ethynyl) cyclohexan-1-ol]

To a solution of trans-[4-(3-cyclopentyloxy-4-methoxyphenyl)-4-ethynyl -cyclohexan-1-ol] (0.125 g, 0.40 mmol) and 2-(3-iodophenyl)-5-methyl[1,3,4]oxadiole (0.171 g, 0.60 mmol) in triethylamine (7 mL) under an argon atmosphere were added tetrakis(triphenylphosphine) palladium (0.020 g, 0.017 mmol), copper(I) iodide (0.0042 g, 0.022 mmol) and a small crystal of triphenylphosphine. After heating the mixture at 75° C. for 1.75 h, the reaction was quenched by addition of aqueous ammonium chloride solution, and the solvent was concentrated. The mixture was extracted three times with methylene chloride, and the organic phase was washed with water, was dried (sodium sulfate) and was evaporated. Purification by flash chromatography, eluting with 40 to 50% ethyl acetate in methylene chloride and crystallizing from ethyl ether, provided cis-[4-(3-cyclopentyloxy-4-methoxyphenyl)4-(2-[3-(5-methyl[1,3,4]oxadiazol-2-yl)phenyl]ethynyl) cyclohexan-1-ol] as a white solid (0.119 g, 63%), mp 117.5°–119° C. Anal. ($C_{29}H_{32}N_2O_4 \cdot 1/8H_2O$) calcd: C, 73.36; H, 6.85, N, 5.90 found: C, 73.25; H, 6.94, N, 5.75. $^1$H-NMR (400 MHz, $CDCl_3$) δ 8.12 (s, 1H), 7.98 (d-d, J=1.4 Hz;J=7.9 Hz, 1H), 7.60 (d-d, J=1.3 Hz, J=7.8 Hz, 1H), 7.46 (t, J=7.8 Hz, 1H), 7.19 (d, J=2.2, 1H), 7.10 (d-d, J=2.1 Hz, J=8.5 Hz, 1H), 6.85 (d, J=8.5 Hz, 1H), 4.81 (p, J=4.3 Hz, 1H), 3.85 (s, 3H), 3.73 (m, 1H), 2.63 (s, 3H), 2.2–1.8 (m, 14H), 1.7–1.5 (m, 7H with $H_2O$).

EXAMPLE 30 cis-[4-(3-cyclopentyloxy-4-methoxyphenyl)-4-(2-[3-(5-methyl[1,2,4]oxadiazol-3-yl)phenyl]ethynyl) cyclohexan-1-ol]

To a solution of 4-(3-cyclopentyloxy-4-methoxyphenyl)-4-(2-[3-(5-methyl[1,2,4]oxadiazol-3-yl)phenyl]ethynyl) cyclohexan-1-one (0.084 g, 0.18 mmol, prepared as described in co-pending application P50283 filed on even date herewith) in 1,2-dimethoxyethane (3 mL) under an argon atmosphere was added dropwise a solution of sodium borohydride (0.015 g, 0.40 mmol) in 1,2-dimethoxyethane (5 mL). After 2 h stirring at room temperature, the reaction was quenched by addition of aqueous ammonium chloride solution. The solvent was concentrated and the residue was extracted into methylene chloride, was washed with water, was dried (sodium sulfate) and was evaporated. Purification by flash chromatography, eluting with 35% ethyl acetate in hexanes and crystallizing from ethyl ether, provided cis-[4-(3-cyclopentyloxy-4-methoxyphenyl)-4-(2-[3-(5-methyl[1,2,4]oxadiazol-3-yl)phenyl]ethynyl)cyclohexan-1-ol] as a white solid (0.050 g, 58%), mp 101°–103° C. Anal. ($C_{29}H_{32}N_2O_4 \cdot 1/5H_2O$) calcd: C, 73.15; H, 6.86, N, 5.88 found: C, 73.11; H, 6.85, N, 5.85. $^1$H-NMR (400 MHz, $CDCl_3$) δ 8.18 (s, 1H), 8.00 (d, J=7.9 Hz, 1H), 7.58 (d, J=7.8 Hz, 1H), 7.43 (t, J=7.8 Hz, 1H), 7.19 (d, J=2.2, 1H), 7.10 (d-d, J=2.1 Hz, J=8.5 Hz, 1H), 6.85 (d, J=8.5 Hz, 1H), 4.82 (p, J=4.3 Hz, 1H), 3.85 (s, 3H), 3.72 (m, 1H), 2.67 (s, 3H), 2.2–1.8 (m, 13H), 1.7–1.5 (m, 6H with $H_2O$).

The other compounds of this invention may be prepared by proceeding in a similar manner, but substituting the appropriate starting materials and intermediates for those recited in this Example. Examples are:

cis-[4-(3-cyclopentyloxy-4-methoxyphenyl)-4-(2-[3-(5-trifluoromethyl[1,2,4]oxadiazol-3-yl)phenyl]ethynyl) cyclohexan-1-ol], cis-[4-(3-cyclopentyloxy-4-methoxyphenyl)-4-(2-[3-(3-trifluoromethyl[1,2,4]oxadiazol-5-yl)phenyl]ethynyl) cyclohexan-1-ol], cis-[4-(3-cyclopentyloxy-4-methoxyphenyl)-4-(2-[3-(5-trifluoromethyl[1,3,4]oxadiazol-2-yl)phenyl]ethynyl) cyclohexan-1-ol], and cis-[4-(3-cyclopentyloxy-4-methoxyphenyl)-4-(2-[3-(5-trifluoromethyl[1,3,4]thiadiazol-2-yl)phenyl]ethynyl) cyclohexan-1-ol].

EXAMPLE 31

Preparation of cis-4-(3-Cyclopentyloxy-4-methoxyphenyl)-4-[3-(5-trifluoromethyl -[1.2.4] oxadiazol-3-yl)phenylethynyl)cyclohexan-1-ol 31a) 3-(3-iodophenyl)-5-trifluoromethyl-[1,2,4]oxadiazole 3-(3-Iodophenyl-5-trifluoromethyl-[1,2,4]oxadiazole was prepared by standard chemistry well known to those versed in the art and was a white solid, mp 36°–37° C.

31b) cis-4-(3-Cyclopentyloxy-4-methoxyphenyl)-4-[3-(5-trifluoromethyl -[1,2,4]oxadiazol-3-yl)phenylethynyl) cyclohexan-1-ol A stirred mixture of trans-[4(3-cyclopentyloxy-4-methoxyphenyl)-4-ethynyl -cyclohexan-1-ol] (0.22 g, 0.7 mmol) and 3-(3-iodophenyl)-5-trifluoromethyl -[1,2,4] oxadiazole (0.24 g, 0.7 mmol) in dry triethylamine (5 mL) was treated under an argon atmosphere trace tetrakis (triphenylphosphine)palladium and copper(I) iodide. The mixture was refluxed for 0.2 h, was cooled to RT and was evaporated. The residue was adsorbed onto silica gel and was purified by flash chromatography eluting with 1:1 hexanes/ethyl acetate and trituration from hexanes/ethyl acetate provided the title compound as a white solid (0.26 g, 71%), mp 8°–86° C.

EXAMPLE 32

Preparation of cis-4-(3-cyclopentyloxy-4-methoxyphenyl)-4-[3-(5-methyl -[1,3,4]thiadiazol-2-yl)phenylethynyl]cyclohexan-1-ol 32a) 1-iodo-3-(5-methyl-[1,3,4]thiadiazol-2-yl)benzene 1-Iodo-3-(5-methyl-[1,3,4]thiadiazol-2-yl)benzene was prepared by standard chemistry well known to those versed in the art and was white solid, m.p. 8°–89° C.

32b) 4-(3-cyclopentyloxy-4-methoxyphenyl)-4-[3-(5-methyl-[1,3,4]thiadiazol-2-yl)phenylethynyl]cyclohexan-1-ol To a solution of trans-[4-(3-cyclopentyloxy-4-methoxyphenyl)-4-ethynyl -cyclohexan-1-ol] (0.15 g, 0.48 mmol) and 1-iodo-3-(5-methyl-[1,3,4]thiadiazol-2-yl) benzene (0.15 g, 0.48 mmol) in triethylamine (5 mL) under an argon atmosphere was added trace tetrakis (triphenylphosphine)palladium(0) and copper(I) iodide. The mixture was refluxed for 0.20 h, was cooled to room temperature and was concentrated in vacuo. Purification by flash chromatography, eluting with 1:1 hexanes/ethyl acetate and trituration from hexanes/ethyl acetate provided the title compound as a white solid (0.17 g, 74%), m.p. 129°–130° C.

EXAMPLE 33

Preparation of trans-[4-(2-acetamidopyrimidin-5-ylethynyl)-4-(3-cyclopentyloy-4-methoxyphenyl) cyclohexan-1-ol]

To a suspension of cis-[4-(3-cyclopentyloxy-4-methoxyphenyl)-4-ethynyl -cyclohexan-1-ol] (0.50 g, 1.59 mmol) and 2-acetamido-5-bromopyrimidine (0.35 g, 1.59 mmol) in triethylamine (7 mL) under an argon atmosphere was added tetrakis(triphenylphosphine)palladium(0) (0.073 g, 4%) and copper(I) iodide (0.019 g, 6%) and the mixture was heated at 80°–85° C. for 0.75 h. Water was added and the mixture was extracted three times with dichloromethane, was dried (magnesium sulfate) and was evaporated. The residue was pre-adsorbed onto silica and purified by chromatography on silica gel, eluting the nonpolar impurities with 30:70 to 50:50 ethyl acetate:dichloromethane, and eluting the desired product in 60:40:1 ethyl acetate:dichloromethane:methanol. This was crystallized from ethyl acetate:hexanes to provide trans-[40(2-acetamidopyrimidin-5-yl-ethynyl)-4-(3-cyclopentyloxy-4-methoxyphenyl) cyclohexan-1-ol] as a white solid (0.47 g, 66%), mp 163°–164° C. Anal. ($C_{26}H_{31}N_3O_4$ 0.25 $H_2O$) calcd:VC, 69.47; H, 6.95; n, 9.35; found: C, 69.27; H, 6.98; N, 8.97.

EXAMPLE 34

Preparation of trans-[4-(2-aminopyrimidin-5-yl-ethynyl)-4-(3-cyclopentyloxy-4-methoxyphenyl)-cyclohexan-1-ol To a solution of sodium methoxide (0.137 g, 2.5 mmol) in dry methanol (3.8 mL) was added via cannula a solution of trans-[4-(2-acetamidopyrimidin-5-ylethynyl) -4-(3-cyclopentyloxy-4-methoxyphenyl)cyclohexan-1-ol] (0.32 g, 0.71 mmol) in dry methanol (7.6 mL including rinses). After stirring for 3 h at 25° C., the reaction was quenched into cold water, extracted with methylene chloride, filtered, dried (magnesium sulfate) and concentrated in vacuo. The resulting solid was recrystallized from ethyl acetate:hexanes and dried in vacuo at 80° C. to afford the desired product as a white solid (0.154 g, 53%), mp 170.5°–172.0° C. Anal. ($C_{24}H_{29}N_3O_3$ 0.125 $H_2O$) calcd: C, 70.35; H, 7.20; N, 10.25; found: C, 70.34; H, 7.18; N, 10.14.

EXAMPLE 35

Preparation of cis-[4-(2-methylaminopyrimidin-5-ylethynyl)-4-(3-cyclopentyloxy-4-methoxyphenyl) cyclohexan-1-ol ]

35(a) 5-bromo-2-methylacetamidopyrimidine,

A mixture of 2-acetamido-5-bromopyrimidine (0.22 g, 1 mmol,) potassium carbonate (0.21 g, 1.5 mmol) and iodomethane (0.10 mL, 1.6 mmol) in tetrahydrofuran was stirred at room temperature for three days. The mixture was filtered, was evaporated and was purified by flash chromatography, eluted with 2:8 ethyl acetate:hexanes, to provide the desired product a a white solid (0.03 g, 13%) $^1$H-NMR (CDCl$_3$, 400 Mhz) δ 8.58 (s, 2H), 3.39 (s, 3H), 2.39 (s, 3H) ppm.
37b) cis-[4-(2-methylacetamidopyrimidin-5-yl-ethynyl)-4-(3-cyclopentyloxy-4-methoxyphenyl)-cyclohexan-1-ol], To a suspension of trans-[4-(3-cyclopentyloxy-4-methoxyphenyl)-4-ethynyl -cyclohexan-1-ol) (0.20 g, 0.64 mmol) and a mixture (~6:4) of 2-acetamido-5-bromopyrimidine and 5-bromo-2-methylacetamidopyrimidine (0.14 g, ~0.32 mmol of each component) in triethylamine (5 mL) under an argon atmosphere was added tetrakis(triphenylphosphine)palladium(0) (0.03 g, 4%) and copper(I) iodide (0.008 g, 6%) and the mixture was heated at 80°–85° C. for 0.5 h. The reaction was cooled, water was added and the mixture was extracted three times with dichloromethane, was dried (magnesium sulfate) and was evaporated. The residue was purified by chromatography on silica gel with 1:1 and 1:3 ethyl acetate:hexanes, to provide the desired compound as a colorless oil (which contains a trace amount of 2-acetamido-5-bromopyrimidine). $^1$H-NMR (CDCl$_3$, 400 Mhz) δ 8.65 (s, 2H), 7.12 (d, J=2.0 Hz, 1H), 7.07 (dd, J=8.3, 2.0 Hz, 1H), 6.85, d, J=8.3Hz, 1H), 4.80 (m, 1H), 3.85 (s, 3H), 3.83 (m, 1H), 3.49 (s, 3H), 2.48 (s, 3H), 1.8–2.2 (m, 14H), 1.65 (m, 2H) ppm.
37c) cis-[4-(2-methylaminopyrimidin-5-ylethynyl)-4-(3-cyclopentyloxy-4-methoxyphenyl)cyclohexan-1-ol]

To a stirred mixture of sodium methoxide (0.025 g, 0.43 mmol) in dry methanol (2 mL) under an argon atmosphere was added a solution of cis-4(2-methylacetamidopyrimidin-5-ylethynyl)-4-(3-cyclopentyloxy-4-methoxyphenyl) cyclohexan-1-ol (0.07 g, 0.15 mmol). The mixture was refluxed for 0.5 h, was cooled to room temperature, was diluted with water, was extracted three times with dichloromethane, was dried (magnesium sulfate) and was evaporated. Purification by flash chromatography, eluting with 3:1 ethyl acetate:hexanes, followed by trituration from ethyl acetate/hexanes, provided the title compound as a white solid (0.032 g, 61%), m.p. 118°–119° C. Anal. ($C_{25}H_{31}N_3O_3$ 0.75 $H_2O$) calcd:C, 69.02; H, 7.52; N, 9.66; found: C, 68.84; H, 7.11; N, 9.53.

EXAMPLE 36

Preparation of trans-[4-(2-aminopyrimidin-5-ylethynyl)-4-(3-cyclopentyloxy-4-methoxyphenyl) cyclohexyl-1-amine], cyclohexylsulfamate salt 34a) 5-bromo-2-propionamidopyrimidine 5-Bromo-2-propionamidopyrimidine was prepared by standard chemistry well known to those versed in the art and was a white solid, mp 161°–164° C.
34b) trans-[1-tert-butoxycarbonylamino-4-cyclopentyloxy-4-methoxyphenyl)-4-(2-propionamidopyrimidine-5-ylethynyl-cyclohexane]

To a solution of cis-[1-tert-butoxycarbonylamino-4-(3-cyclopentyloxy-4-methoxyphenyl)-4-ethynylcyclohexane] (0.29 g, 0.69 mmol) and 5-bromo-2-propionamidopyrimidine (0.16 g, 0.69 mmol) in triethylamine (5 mL) under an argon atmosphere were added tetrakis(triphenylphosphine)palladium(0) (0.032 g, 4%), and copper(I) iodide (0.008 g, 6%) and the mixture was heated at 80°–85° C. for 0.5 h. Water was added and the mixture was extracted three times with dichloromethane, was dried (magnesium sulfate) and was evaporated. Purification by flash chromatography, eluting with 35:65 ethyl acetate:hexanes, provided trans-[1tert-butoxycarbonylamino -4-(3-cyclopentyloxy-4-methoxyphenyl)-4-(2-propionamidopyrimidin-5-ylethynyl) -cyclohexane] as a white solid (0.21 g, 54%), mp 87°–89° C. $^1$H-NMR (400 MHz, CDCl$_3$) δ 8.57 (s, 2H), 8.17 (m, 1H), 7.11 (d, J=2.2 Hz, 1H), 7.03 (dd, J=8.5, 2.2 Hz, 1H), 6.86 (d, J=8.5 Hz, 1H), 4.81 (m, 1H), 4.63 (m, 1H), 3.85 (s, 3H), 2.75 (q, J=7.4 Hz, 2H), 1.8–2.1 (m, 14H), 1.62 (m, 2H), 1.46, (s, 9H), 1.24 (t, J=7.4 Hz, 3H) ppm.
34c) trans-[4-(2-aminopyrimidin-5-ylethynyl)-1-tert-butoxycarbonylamino-4-(3-cyclopentyloxy-4-methoxyphenyl)cyclohexane]

A mixture of trans-[1-tert-butoxycarbonylamino-4-(3-cyclopentyloxy-4-methoxyphenyl)-4-(2-propionamidopyrimidin-5-ylethynyl)cyclohexane] (0.21 g, 0.37 mmol) and sodium methoxide (0.07 g, 1.29 mmol) in methanol (5 mL) was refluxed under an argon atmosphere for 0.5 h, then cooled. Water was added and the reaction was extracted three times with dichloromethane was dried (magnesium sulfate) and was evaporated to provide pure trans-[4-(2-aminopyrimidin-5-ylethynyl)-1-tert -butoxycarbonylamino-4-(3-cyclopentyloxy-4-methoxyphenyl) cyclohexane] (0.18 g, 97%) as a white solid mp 183°–185° C. $^1$H-NMR (400 MHz, CDCl$_3$) δ 8.34 (s, 2H), 7.13 (d, J=2.3 Hz, 1H), 7.03 (dd, J=8.5, 2.3 Hz 1H), 6.86 (d, J=8.5 Hz, 1H) 5.27 (d, J=2.2 Hz, 2H), 4.81 (m, 1H), 4.64 (m, 1H), 3.85 (s, 3H), 1.8–2.1 (m, 14H), 1.61 (m, 2H), 1.46 (s, 9H) ppm.

34d) trans-[4-(2-aminopyrimidin-5-ylethynyl)-4-(3-cyclopentyloxy-4-methoxyphenyl)cyclohexyl-1-amine], cyclohexylsulfamate salt To a solution of trans-[4-(2-aminopyrimidin-5-ylethynyl)-1-tert-butoxycarbonylamino-4-(3-cyclopentyloxy-4-methoxyphenyl) cyclohexane] (0.18 g, 0.35 mmol) in dichloromethane (5 mL) at 0° C. under an argon atmosphere was added trifluoroacetic acid (0.27 mL, 3.52 mmol). The reaction was stirred at room temperature for 24 h, was cooled to 0° C., was quenched with sodium bicarbonate, was diluted with water, was extracted with three times 10/90 methanol/dichloromethane, was dried (magnesium sulfate) and was evaporated. Purification by flash chromatography, eluting with 0.5:10:90 ammonium hydroxide:methanol:dichloromethane provided trans[4-(2-aminopyrimidin-5-ylethynyl)-4-(3-cyclopentyloxy-4-methoxyphenyl) cyclohexyl-1-amine] as a very viscous, colorless oil (0.13 g, 0.33 mmol, 95%). This intermediate was dissolved in acetone (0.5 mL) and treated with a solution of cyclohexylsulfamic acid (0.059 g, 0.33 mmol) in acetone (1.0 mL). Dilution with ether and filtration, followed by trituration from dichloromethane/hexanes provided the title compound as a white solid, mp >230° C. (dec.).

EXAMPLE 37 cis-[4-(2-aminopyrimidin-5-ylethynyl)-4-(3-cyclopentyloxy-4-methoxyphenyl)cyclohexyl-1-amine], cyclohexylsulfamate salt cis-[4-(2-aminopyrimidin-5-ylethynyl)-4-(3-cyclopentyloxy-4-methoxyphenyl)cyclohexyl-1-amine], cyclohexylsulfamate salt is prepared in the same manner as trans-[4-(2-aminopyrimidin-5-ylethynyl)-4-(3-cyclopentyloxy-4-methoxyphenyl)cyclohexyl-1-amine], except starting from cis -[1-tert-butoxycarbonylamino-4-(3-cyclopentyloxy-4-methoxyphenyl)-4-ethynyl-cyclohexane].

UTILITY EXAMPLES

EXAMPLE A

Inhibitory effect of compounds of Formula (I) on in vitro TNF production by human monocytes The inhibitory effect of compounds of Formula (I) on in vitro TNF production by human monocytes may be determined by the protocol as described in Badger et al., EPO published Application 0 411 754 A2, Feb. 6, 1991, and in Hanna, WO 90/15534, Dec. 27, 1990.

EXAMPLE B

Two models of endotoxic shock have been utilized to determine in vivo TNF activity for the compounds of Formula (I). The prototocol used in these models is described in Badger et al., EPO published Application 0 411 754 A2, Feb. 6, 1991, and in Hanna, WO 90/15534, Dec. 27, 1990.

The compound of Example 1 herein demonstrated a positive in vivo response in reducing serum levels of TNF induced by the injection of endotoxin.

EXAMPLE C

Isolation of PDE Isozymes

The phosphodiesterase inhibitory activity and selectivity of the compounds of Formula (I) can be determined using a battery of five distinct PDE isozymes. The tissues used as sources of the different isozyme s are as follows: 1) PDE Ib, porcine aorta; 2) PDE Ic, guinea-pig heart; 3) PDE III, guinea-pig heart; 4) PDE IV, human monocyte; and 5) PDE V (also called "Ia"), canine trachealis. PDEs Ia, Ib, Ic and III are partially purified using standard chromatographic techniques [Torphy and Cieslinski, Mol. Pharmacol., 37:206–214, 1990]. PDE IV is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive IC$_{50}$'s in the nanomolar to μM range for compounds of the workings examples described herein for Formula (I) have been demonstrated.

What is claimed is:

1. A compound of Formula I

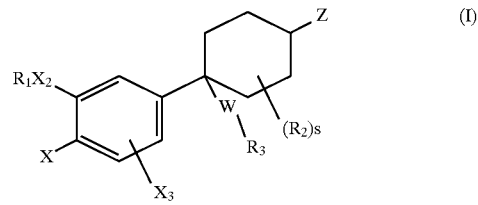

wherein:

$R_1$ is —(CR$_4$R$_5$)$_n$C(O)O(CR$_4$R$_5$)$_m$R$_6$, —(CR$_4$R$_5$)$_n$C(O)NR$_4$(CR$_4$R$_5$)$_m$R$_6$, —(CR$_4$R$_5$)$_n$O(CR$_4$R$_5$)$_m$R$_6$, or —(CR$_4$R$_5$)$_r$R$_6$ wherein the alkyl moieties unsubstituted or substituted with one or more halogens;

m is 0 to 2;

n is 0 to 4;

r is 0 to 6;

$R_4$ and $R_5$ are independently selected hydrogen or $C_{1-2}$ alkyl;

$R_6$ is hydrogen, methyl, hydroxyl, aryl, halo substituted aryl, aryloxy $C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, one ethyl group, or an hydroxyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in —(CR$_4$R$_5$)$_n$O(CR$_4$R$_5$)$_m$R$_6$;

X is YR$_2$, fluorine, NR$_4$R$_5$, or formyl amine;

Y is O or S(O)$_{m'}$;

m' is 0, 1, or 2;

$X_2$ is O or NR$_8$;

$X_3$ is hydrogen or X;

$R_2$ is independently selected from —CH$_3$ or —CH$_2$CH$_3$ optionally substituted by 1 or more halogens;

s is 0 to 4;

W is alkyl of 2 to 6 carbons, alkenyl of 2 to 6 carbon atoms or alkynyl of 2 to 6 carbon atoms;

$R_3$ is $COOR_{14}$, $C(O)NR_4R_{14}$ or $R_7$;

Z is $OR_{14}$, $OR_{15}$, $SR_{14}$, $S(O)_m{'}R_7$, $SO_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$;

Y' is O or S;

$R_7$ is $-(CR_4R_5)_qR_{12}$ or $C_{1-6}$ alkyl wherein the $R_{12}$ or $C_{1-6}$ alkyl group is unsubstituted or substituted one or more times by methyl or ethyl unsubstituted or substituted by 1–3 fluorines; —F, —Br, —Cl, —NO$_2$, —NR$_{10}$R$_{11}$, —C(O)R$_8$, —CO$_2$R$_8$, —O(CH$_2$)$_{2-4}$OR$_8$, —O(CH$_2$)$_q$R$_8$, —CN, —C(O)NR$_{10}$R$_{11}$, —O(CH$_2$)$_q$C(O)NR$_{10}$R$_{11}$, —O(CH$_2$)$_q$C(O)R$_9$, —NR$_{10}$C(O)NR$_{10}$R$_{11}$, —NR$_{10}$C(O)R$_{11}$, —NR$_{10}$C(O)OR$_9$, —NR$_{10}$C(O)R$_{13}$, —C(NR$_{10}$)NR$_{10}$R$_{11}$, —C(NCN)NR$_{10}$R$_{11}$, —C(NCN)SR$_9$, —NR$_{10}$C(NCN)SR$_9$, —NR$_{10}$C(NCN)NR$_{10}$R$_{11}$, —NR$_{10}$S(O)$_2$R$_9$, —S(O)$_m{'}$R$_9$, —NR$_{10}$C(O)C(O)NR$_{10}$R$_{11}$, —NR$_{10}$C(O)C(O)R$_{10}$, or R$_{13}$;

q is 0, 1, or 2;

$R_{12}$ is $R_{13}$, $C_3$–$CH_7$ cycloalkyl, or an unsubstituted or substituted aryl or heteroaryl group selected from the group consisting of (2-, 3- or 4-pyridyl), pyrimidyl, pyrazolyl, (1- or 2-imidazolyl), pyrrolyl, piperazinyl, piperidinyl, morpholinyl, furanyl, (2- or 3-thienyl), quinolinyl, naphthyl, and phenyl;

$R_8$ is independently selected from hydrogen or $R_9$;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised of carbon or carbon and one or more additional heteroatoms selected from O, N, or S;

$R_{13}$ is a substituted or unsubstituted heteroaryl group selected from the group consisting of oxazolidinyl, oxazolyl, thiazolyl, pyrazolyl, triazolyl, tetrazolyl, imidazolyl, imidazolidinyl, thiazolidinyl, isoxazolyl, oxadiazolyl, and thiadiazolyl, and where $R_{13}$ is substituted on $R_{12}$ or $R_{13}$ the rings are connected through a carbon atom and each second $R_{13}$ ring may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring comprised of carbon or carbon and one or more additional heteroatoms selected from O, N, or S;

$R_{15}$ is $C(O)R_{14}$, $C(O)NR_8R_{14}$, $S(O)_qNR_8R_{14}$ or $S(O)_qR_7$ where q is 0, 1 or 2;

provided that:

(f) $R_7$ is not $C_{1-4}$ alkyl unsubstituted or substituted by one to three fluorines; and (g) provided that W is not ethyl when $R_3$ is $R_7$ where $R_7$ is $NR_{10}R_{11}$ where $R_{10}$ and $R_{11}$ are methyl or ethyl; X is $YR_2$ where Y is O and $R_2$ is methyl; $X_2$ is O, $R_1$ is $(CR_4R_5)_rR_6$ where r is 0 and $R_6$ is methyl; and s is 0;

or the pharmaceutically acceptable salts thereof.

2. A compound according to claim 1 wherein $R_1$ is —CH$_2$-cyclopropyl, —CH$_2$-C$_{5-6}$ cycloalkyl, —C$_{4-6}$ cycloalkyl unsubstituted or substituted by OH, tetrahydrofuran-3-yl, (3-or 4-cyclopentenyl), benzyl or —C$_{1-2}$ alkyl unsubstituted or substituted by 1 or more fluorines, and —(CH$_2$)$_{2-4}$ OH; $R_2$ is methyl or fluoro-substituted alkyl, W is ethynyl or 1,3-butadiynyl, $R_3$ is $R_7$ where $R_7$ is an unsubstituted or substituted aryl or heteroaryl heteroaryl ring, X is $YR_2$, and Z is $OR_{14}$, $OR_{15}$, $NR_{10}R_{14}$, or $NR_{14}C(O)R_9$.

3. A compound according to claim 2 wherein $R_7$ is unsubstituted or substituted —(CH$_2$)$_{0-2}$(2-, 3- or 4-pyridyl), (C$_2$)$_{1-2}$(2-imidazolyl), (CH$_2$)$_2$(4morpholinyl), (CH$_2$)$_2$(4-piperazinyl), (CH$_2$)$_{1-2}$(2-thienyl), (CH$_2$)$_{1-2}$(4-thiazolyl), substituted or unsubstituted pyrimidinyl, or unsubstituted or substituted (CH$_2$)$_{0-2}$phenyl.

4. A compound according to claim 3 wherein $R_7$ is substituted or unsubstituted pyrimidin-5-yl.

5. A compound according to claim 4 wherein Z is OH and which is cis-[4-(2-aminopyrimidin-5-ylethynyl)-4-(3-cyclopentyloxy-4-methoxyphenyl)cyclohexan-1-ol], cis-[4-(2-aminopyrimidin-4-ylethynyl)-4-(3-cyclopentyloxy-4-methoxyphenyl)-cyclohexan-1-ol], trans-[4-(2-acetamidopyrimidin-5-ylethynyl)-4-(3-cyclopentyloy-4-methoxyphenyl)cyclohexan-1-ol], trans-[4-(2-aminopyrimidin-5-yl-ethynyl)-4-(3-cyclopentyloxy-4-methoxyphenyl)cyclohexan-1-ol], or cis-[4-(2-methylaminopyrimidin-5-ylethynyl)-4-(3-cyclopentyloxy-4-methoxyphenyl)cyclohexan-1-ol].

6. A compound according to claim 1, 2 or 3 wherein Z is OH and which is cis-[4-(3-cyclopentyloxy-4-methoxyphenyl)-4-(pyrid-4-ylethynyl)cyclohexan-1-ol], cis-[4-(3-cyclopentyloxy-4-methoxyphenyl)-4-(pyrid-2-ylethynyl)cyclohexan-1-ol], cis-[4-(4-cyanothien-2-ylethynyl)-4-(3-cyclopentyloxy-4-methoxyphenyl)cyclohexan-1-ol], cis-[4-(thiazol-2-ylethynyl)-4-(3-cyclopentyloxy-4-methoxyphenyl)cyclohexan-1-ol], cis-[4-(3-cyclopentyloxy-4-methoxyphenyl)-4-[5-(5-methyl-[1,2,4]oxadiazol-2-yl)thien-2-ylethynyl]cyclohexan-1-ol], cis-[4-(3-cyclopentyloxy-4-methoxyphenyl)-4-(2-[3-(3-methyl[1,2,4]oxadiazol-5-yl)phenyl]ethynyl)cyclohexan-1-ol], cis-[4-(3-cyclopentyloxy-4-methoxyphenyl)-4-(2-[3-(5-methyl[1,3,4]oxadiazol-2-yl)phenyl]ethynyl)cyclohexan-1-ol], cis-[4-(3-cyclopentyloxy-4-methoxyphenyl)-4-(2-[3-(5-methyl [1,2,4]oxadiazol-3-yl)phenyl]ethynyl)cyclohexan-1-ol], cis-4-(3-cyclopentyloxy-4-methoxyphenyl)-4-[3-(5-trifluoromethyl-[1,2,4]oxadiazol-3-yl)phenylethynyl)cyclohexan-1-ol], or cis-4-(3-cyclopentyloxy-4-methoxyphenyl)-4-[3-(5-methyl-[1,3,4]thiadiazol-2-yl)phenylethynyl]cyclohexan-1-ol.

7. A compound according to claim 1, 2 or 3 wherein Z is $NR_{10}R_{14}$, or $NR_{14}C(O)R_9$ which is trans-[4-(3-cyclopentyloxy-4-methoxphenyl)-4-(pyrid-2-ylethynyl)cyclohexyl-1-amine], trans-[4-(3-cyclopentyloxy-4-methoxyphenyl)-4-(pyrid-2-ylethynyl)cyclohexyl-1-formamide], trans-[4-(3-cyclopentyloxy-4-methoxylphenyl)-4-[5-(5-methyl-[1,2,4]oxadiazol-2-yl)thien-2-ylethynyl] cyclohexy-1-amine], cyclohexylsulfamate salt cis-[4-(3-cyclopentyloxy-4-methoxyphenyl)-4-(pyrid-2-ylethynyl)cyclohexyl-1-amine], cis-[4-(3-cyclopentyloxy-4-methoxyphenyl)-4-(pyrid-2-ylethynyl)cyclohexyl-1-formamide], cis-[4-(3-cyclopentyloxy-4-methoxyphenyl)-4-[5-(5-methyl-[1,2,4]oxadiazol-2-yl)thien-2-ylethynyl]cyclohexyl-1-amine], cyclohexylsulfamate salt, trans-[4-(2-aminopyrimidin-5-ylethynyl)-4-(3-cyclopentyloxy-4-methoxyphenyl)cyclohexyl-1-amine], cyclohexylsulfamate salt, or cis-[4-(2-aminopyrimidin-5-ylethynyl)-4-(3-cyclopentyloxy-4-methoxyphenyl)cyclohexyl-1-amine], cyclohexylsulfamate salt.

8. A pharmaceutical composition comprising a compound of Formula I according to any one of claims 1 to 7 and a pharmaceutically acceptable excipient.

9. A method for treating asthma which comprises administering to a mammal in need thereof a compound of formula (I) according to any one of claims 1 to 7 alone or admixed with a pharmaceutically acceptable excipient.

* * * * *

UNITED STATES PATENT AND TRADEMARK OFFICE
CERTIFICATE OF CORRECTION

PATENT NO. : 5,891,883  
DATED : April 6, 1999  
INVENTOR(S) : Christensen, et al.

Page 1 of 1

It is certified that error appears in the above-identified patent and that said Letters Patent is hereby corrected as shown below:

<u>Claim 6,</u>
Line 32, please delete ",2 or 3".

<u>Claim 7,</u>
Line 59, please delete ",2 or 3".

<u>Claim 8,</u>
Line 5, please delete "any one of claims 1 to 7" and replace with "claim 1".

<u>Claim 9,</u>
Line 9, please delete "any one of claims 1 to 7" and replace with "claim 1".

Signed and Sealed this

Fourteenth Day of August, 2001

*Attest:*

NICHOLAS P. GODICI
*Attesting Officer*   *Acting Director of the United States Patent and Trademark Office*